US011185221B2

(12) United States Patent
Saika et al.

(10) Patent No.: US 11,185,221 B2
(45) Date of Patent: Nov. 30, 2021

(54) OPHTHALMOLOGIC INFORMATION PROCESSING APPARATUS, OPHTHALMOLOGIC APPARATUS, AND OPHTHALMOLOGIC INFORMATION PROCESSING METHOD

(71) Applicant: TOPCON CORPORATION, Tokyo (JP)

(72) Inventors: Makoto Saika, Nerima-ku (JP); Tsutomu Kikawa, Adachi-ku (JP)

(73) Assignee: TOPCON CORPORATION, Tokyo (JP)

( * ) Notice: Subject to any disclaimer, the term of this patent is extended or adjusted under 35 U.S.C. 154(b) by 203 days.

(21) Appl. No.: 16/540,085

(22) Filed: Aug. 14, 2019

(65) Prior Publication Data

US 2020/0093363 A1    Mar. 26, 2020

(30) Foreign Application Priority Data

Sep. 25, 2018  (JP) .............................. JP2018-179139

(51) Int. Cl.
*A61B 3/10*     (2006.01)
*A61B 3/12*     (2006.01)
(Continued)

(52) U.S. Cl.
CPC ................ *A61B 3/102* (2013.01); *A61B 3/12* (2013.01); *A61B 3/152* (2013.01); *A61B 3/103* (2013.01); *A61B 3/145* (2013.01); *A61B 3/158* (2013.01)

(58) Field of Classification Search
CPC ........... A61B 3/102; A61B 3/12; A61B 3/152; A61B 3/103; A61B 3/145; A61B 3/158; A61B 3/0025; A61B 3/107; A61B 5/0066
(Continued)

(56) References Cited

U.S. PATENT DOCUMENTS 9,204,793 B2 * 12/2015 Iwanaga ............... A61B 3/1225
2012/0002164 A1   1/2012 Yamamoto et al.
(Continued)

FOREIGN PATENT DOCUMENTS

CN     107438392 A    12/2017
EP     2 404 545 A2    1/2012
(Continued)

OTHER PUBLICATIONS

Extended European Search Report dated Feb. 24, 2020, issued in corresponding European Patent Application No. 19195050.0.
(Continued)

*Primary Examiner* — Mohammed A Hasan
(74) *Attorney, Agent, or Firm* — Xsensus LLP

(57) ABSTRACT

An ophthalmologic apparatus includes an OCT measurement unit, a corneal shape measurement unit, an eyeball model generator, and a site specifying unit. The OCT measurement unit is configured to acquire data of a subject's eye by deflecting measurement light using an optical scanner to project onto the subject's eye and detecting interference light between returning light of the measurement light from the subject's eye and reference light. The corneal shape measurement unit is configured to obtain curvature radius distribution on a cornea by detecting returning light of a measurement pattern projected onto a cornea of the subject's eye. The eyeball model generator is configured to generate an eyeball model using the curvature radius distribution on the cornea. The site specifying unit is configured to specify a traveling direction of the measurement light by performing ray tracing on the measurement light incident on each of a plurality of incident positions on the cornea based on a scan angle and the eyeball model, and to specify a position corresponding to an intraocular site of the subject's eye in
(Continued)

the traveling direction based on the data acquired using the measurement light.

8 Claims, 8 Drawing Sheets

(51) Int. Cl.
*A61B 3/15* (2006.01)
*A61B 3/103* (2006.01)
*A61B 3/14* (2006.01)

(58) Field of Classification Search
USPC .......................................................... 351/206
See application file for complete search history.

(56) References Cited

U.S. PATENT DOCUMENTS

| | | |
|---|---|---|
| 2012/0069298 A1 | 3/2012 | Ng |
| 2012/0189184 A1 | 7/2012 | Matsumoto et al. |
| 2016/0302659 A1 | 10/2016 | Boss et al. |
| 2017/0245756 A1 | 8/2017 | Hayashi et al. |
| 2017/0273558 A1* | 9/2017 | Tamura .................... A61B 3/13 |
| 2018/0084991 A1* | 3/2018 | Shibutani ............. A61B 3/0033 |
| 2018/0310819 A1 | 11/2018 | Boss et al. |
| 2020/0113430 A1 | 4/2020 | Boss et al. |

FOREIGN PATENT DOCUMENTS

| | | | | |
|---|---|---|---|---|
| EP | 2404545 A2 * | 1/2012 | .......... | A61B 3/1025 |
| JP | 5794664 B2 | 10/2015 | | |
| JP | 2016-43155 A | 4/2016 | | |

OTHER PUBLICATIONS

Office Action dated Sep. 1, 2021, in corresponding Chinese patent Application No. 201910843140.8, 13 pages.

* cited by examiner

OPHTHALMOLOGIC INFORMATION PROCESSING APPARATUS, OPHTHALMOLOGIC APPARATUS, AND OPHTHALMOLOGIC INFORMATION PROCESSING METHOD

CROSS-REFERENCE TO RELATED APPLICATION

This application is based upon and claims the benefit of priority from Japanese Patent Application No. 2018-179139, filed Sep. 25, 2018; the entire contents of which are incorporated herein by reference.

FIELD

Embodiments according to present invention described herein relate to an ophthalmologic information processing apparatus, an ophthalmologic apparatus, and an ophthalmologic information processing method.

BACKGROUND

In recent years, attention has been drawn to optical coherence tomography (OCT) which is used to measure the morphology of an object to be measured or to image using light beams emitted from a laser light source or the like. Since OCT does not have invasiveness to human body as X-ray CT (Computed Tomography) does, development of application of OCT in medical field and biology field is particularly expected. For example, in the ophthalmologic field, apparatuses for forming images of the fundus or the cornea have been in practical use.

Such apparatuses using OCT (OCT apparatuses) can be used to observe or measure a variety of sites (fundus, anterior segment) of a subject's eye. In addition, because of the ability to acquire high precision images, the OCT apparatuses are applied to the diagnosis of various eye diseases.

The OCT apparatuses are also expected for applications in the diagnosis of myopia. Myopia is a refractive error in which light beams entering the eyeball focus in front of the retina. In myopia, there is pathological myopia in which it is considered difficult to obtain normal vision even when corrected with glasses or the like. In pathological myopia, the eye axis is long, the posterior part of the eyeball is deformed, and various pathological changes occur in the retina and/or the optic nerve. By observing the shape of the eyeball using an OCT apparatus, it is expected to contribute to the prevention of the progression to pathological myopia.

For example, Japanese Patent No. 5794664 discloses a method for obtaining a real shape of the eyeball from the shape of a fundus (retina) obtained from a tomographic image, by correcting in consideration of optical distances in the tomographic image of the subject's eye and incident angles of light beams by a scan mirror.

SUMMARY

One aspect of the some embodiments is an ophthalmologic apparatus, comprising: an OCT measurement unit including an optical scanner and configured to acquire data of a subject's eye by splitting light from a light source into measurement light and reference light, deflecting the measurement light using the optical scanner to project onto the subject's eye, and detecting interference light between returning light of the measurement light from the subject's eye and the reference light; a corneal shape measurement unit configured to project a measurement pattern onto a cornea of the subject's eye, to detect returning light of the measurement pattern, and to obtain curvature radius distribution on the cornea based on an image formed by the detected returning light; an eyeball model generator configured to generate an eyeball model using the curvature radius distribution on the cornea; and a site specifying unit configured to specify a traveling direction of the measurement light by performing ray tracing on the measurement light incident on each of a plurality of incident positions on the cornea based on a scan angle by the optical scanner and the eyeball model, and to specify a position corresponding to an intraocular site of the subject's eye in the traveling direction based on the data acquired using the measurement light.

Another aspect of some embodiments is an ophthalmologic information processing apparatus for specifying at least a position of an intraocular site of a subject's eye based on data acquired by performing optical coherence tomography on the subject's eye. The ophthalmologic information processing apparatus includes: an eyeball model generator configured to generate an eyeball model using curvature radius distribution on a cornea of the subject's eye; and a site specifying unit configured to specify a traveling direction of measurement light by performing ray tracing on the measurement light incident on each of a plurality of incident positions based on a scan angle of an optical scanner deflecting the measurement light and the eyeball model, and to specify a position corresponding to an intraocular site of the subject's eye in the traveling direction based on the data acquired using the measurement light.

Further another aspect of some embodiments is an ophthalmologic information processing method for specifying a shape of an intraocular site of a subject's eye based on data acquired by performing optical coherence tomography on the subject's eye. The ophthalmologic information processing method includes: an eyeball model generating step that generates an eyeball model using curvature radius distribution on a cornea of the subject's eye; and a site specifying step that specifies a traveling direction of measurement light by performing ray tracing on the measurement light incident on each of a plurality of incident positions based on a scan angle of an optical scanner deflecting the measurement light and the eyeball model, and specifies a position corresponding to an intraocular site of the subject's eye in the traveling direction based on the data acquired using the measurement light.

DETAILED DESCRIPTION

Figure 1:
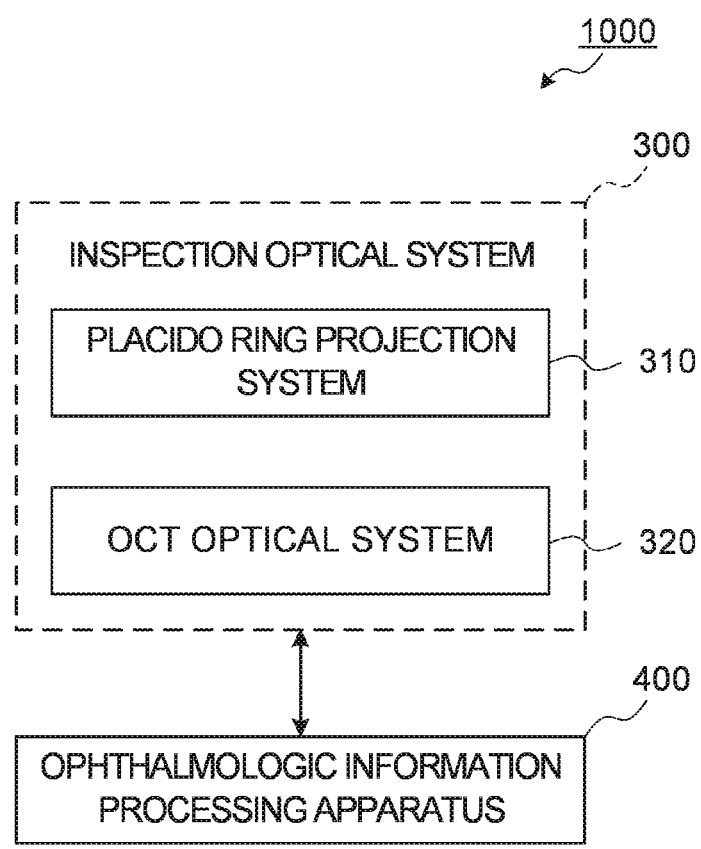
FIG. 1 is a schematic diagram illustrating an example of the configuration of the ophthalmologic apparatus according to embodiments.

In the conventional methods, the shape of the eyeball is obtained on the assumption that the anterior surface of the cornea of the subject's eye is symmetrical with respect to the corneal apex. Thereby, corneal diseases (for example, conical cornea, irregular astigmatism), in which the anterior surface of the cornea is asymmetric with respect to the corneal apex, are not taken into account. Therefore, even when it is judged from the obtained tomographic image that there is an abnormality in the shape of the fundus (the retina, the intraocular site in a broad sense), it is impossible to determine whether the cause is in the cornea or the real cause is in the retina.

According to some embodiments of the present invention, a new technique for accurately obtaining a position and/or a shape of an intraocular site in accordance with a shape of a cornea can be provided.

Referring now to the drawings, exemplary embodiments of an ophthalmologic information processing apparatus, an ophthalmologic apparatus, and an ophthalmologic information processing method according to the present invention are described below. Any of the contents of the documents cited in the present specification and arbitrary known techniques may be applied to the embodiments below.

The ophthalmologic apparatus according to embodiments has the function of the ophthalmologic information processing apparatus. The functions of the ophthalmologic information processing apparatus are realized according to an ophthalmologic information processing program. The ophthalmologic information processing apparatus includes a processor and a storage unit in which the ophthalmologic information processing program is stored in advance. The processor realizes the functions of the ophthalmologic information processing apparatus by executing processing in accordance with the ophthalmologic information processing program read out from the storage unit.

In the ophthalmologic apparatus according to the embodiments, a keratometry (placido measurement), a measurement using optical coherence tomography (hereinafter referred to as OCT), and a photographing using OCT can be performed.

Hereinafter, in the embodiments, the case of using the swept source type OCT method in the measurement and the like using OCT will be described. However, the configuration according to the embodiments can also be applied to an ophthalmologic apparatus using other type of OCT (for example, spectral domain type OCT).

An ophthalmologic apparatus according to some embodiments further includes a subjective inspection optical system for performing subjective inspection and an objective measurement system for performing other objective measurement.

The subjective inspection is a method for measurement to acquire information using the responses from the subject. Examples of the subjective inspection include a visual field test, and a subjective refractometry such as a far vision test, a near vision test, a contrast test, a glare test or the like.

The objective measurement is a method for measurement to acquire information on a subject's eye mainly by the use of a physical method without referring to the responses from the subject. The objective measurements include a measurement for acquiring the characteristics of the subject's eye and a photographing for acquiring an image of the subject's eye. Examples of the other objective measurements include an eye refractive power measurement (refractometry), a tonometry, a fundus photography, and the like.

Hereinafter, a fundus conjugate position is a position substantially optically conjugate with a fundus of the subject's eye in a state where alignment is completed, and means a position optically conjugate with the fundus of the subject's eye or the vicinity of the position. Similarly, a pupil conjugate position is a position substantially optically conjugate with a pupil of the subject's eye in a state where alignment is completed, and means a position optically conjugate with the pupil of the subject's eye or the vicinity of the position.

<Configuration of Ophthalmologic Apparatus>

FIG. 1 shows a schematic diagram of an example of the configuration of an ophthalmologic apparatus 1000 according to the embodiments. The ophthalmologic apparatus 1000 includes an inspection optical system 300 and an ophthalmologic information processing apparatus 400. The inspection optical system 300 includes an optical system for optical inspecting a subject's eye. In FIG. 1, the inspection optical system 300 includes a placido ring projection system 310 and an OCT optical system 320.

The placido ring projection system 310 is an optical system for measuring a corneal shape of the subject's eye. Specifically, the placido ring projection system 310 is configured to project a concentric plurality of ring-shaped patterns (measurement patterns, placido rings) onto the cornea of the subject's eye and to detect returning light of the ring-shaped patterns. The OCT optical system 320 is an optical system for performing OCT on the subject's eye. Specifically, the OCT optical system 320 includes an interference optical system. The OCT optical system 320 is configured to project measurement light onto the subject's eye and to detect interference light between reference light and returning light of the measurement light.

The ophthalmologic information processing apparatus 400 has the function of controlling the inspection optical system 300 and the function of performing predetermined information processing on data acquired by the inspection optical system 300. Examples of the information processing include calculation processing of a measured value of the corneal shape based on the data acquired by the inspection optical system 300, analysis processing on the data acquired by the placido ring projection system 310 or the OCT optical system 320, imaging processing based on the data acquired by the placido ring projection system 310 or the OCT optical system 320, and the like.

In the ophthalmologic apparatus 1000, the keratometry is performed by projecting the placido ring using the placido ring projection system 310, and distribution information of the corneal information on the cornea of the subject's eye is obtained. That is, the corneal information is obtained on each of a plurality of positions on the cornea. In some embodiments, the corneal information includes a corneal curvature radius. The ophthalmologic apparatus 100 performs OCT measurement on a predetermined scan region of a fundus of the subject's eye using the OCT optical system 320, and acquires OCT data. The ophthalmologic information processing apparatus 400 generates an eyeball model using the corneal information corresponding to an incident position of the measurement light on the cornea. In some embodiments, the ophthalmologic information processing apparatus 400 generates the eyeball model by replacing at least one of parameters, which are included in schematic eye data of the schematic eye such as Gullstrand schematic eye, with the measured value using the placido ring projection system 310 for each incident position of the measurement light on the cornea.

The ophthalmologic information processing apparatus 400 specifies a traveling direction of the measurement light by performing ray tracing on the measurement light incident on the cornea based on an incident angle of the measurement light (a scan angle by the optical scanner) and the generated eyeball model, and specifies a position corresponding to an intraocular site in the traveling direction based on the OCT data acquired using the measurement light. In some embodiments, the intraocular site is a retina (fundus). In some embodiments, size information (for example, a value corresponding to the actual size per pixel) at the specified position in the intraocular site is specified based on the schematic data, an eye refractive power of the subject's eye, and an axial length of the subject's eye, and the shape of the intraocular site is specified based on the size information.

In some embodiments, the ophthalmologic apparatus 1000 includes the functions of the ophthalmologic information processing apparatus 400 alone, and acquires the data obtained by performing placido measurement and the data obtained by performing OCT from an external apparatus. In some embodiments, the ophthalmologic apparatus 1000 includes one of the placido ring projection system 310 and the OCT optical system 320, and acquires the data obtained by performing placido measurement or the data obtained by performing OCT from the external apparatus.

<Configuration of Optical System>

Figure 2:
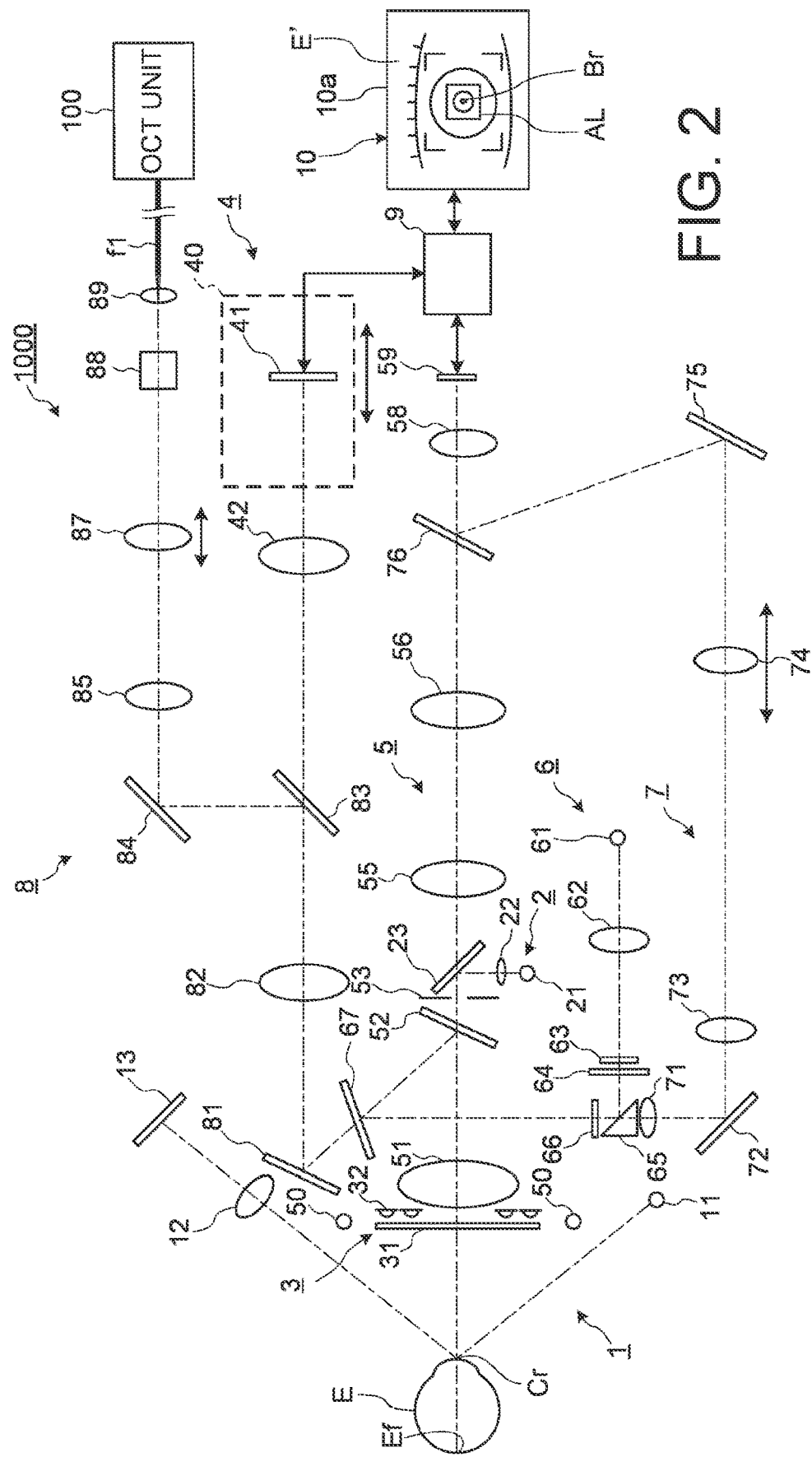
FIG. 2 is a schematic diagram illustrating an example of a configuration of an optical system of the ophthalmologic apparatus according to the embodiments.

FIG. 2 illustrates a configuration example of an optical system of the ophthalmologic apparatus 1000 in FIG. 1. The functions of the placido ring projection system 310 in FIG. 1 are realized by a placido ring projection system 3 in FIG. 2. The functions of the OCT optical system 320 in FIG. 1 are realized by an OCT optical system 8 in FIG. 2. The functions of the ophthalmologic information processing apparatus 400 in FIG. 1 are realized by a processing unit 9 in FIG. 2.

The ophthalmologic apparatus 1000 includes an optical system for observing the subject's eye E, an optical system for inspecting the subject's eye E, and a dichroic mirror that wavelength-separates the optical paths of these optical systems. An anterior segment observation system 5 is provided as the optical system for observing the subject's eye E. An OCT optical system, a placido ring projection system, and a refractometry optical system (eye refractive power measurement optical system) are provided as the optical system for inspecting the subject's eye E.

The ophthalmologic apparatus 1000 includes a Z alignment system 1, a XY alignment system 2, the placido ring projection system 3, a fixation projection system 4, the anterior segment observation system 5, a refractometry projection system 6, a refractometry light reception system 7, and the OCT optical system 8. Hereinafter, for example, it is assumed that light with 940 nm to 1000 nm is used in the anterior segment observation system 5, light with 830 nm to 880 nm is used in the refractometry optical system (refractometry projection system 6, refractometry light reception system 7), light with 400 nm to 700 nm is used in the fixation projection system 4, and light with 1000 nm to 1100 nm is used in the OCT optical system 8. The placido ring projection system 3 can use light in the same wavelength range as that of the refractometry optical system.

(Anterior Segment Observation System 5)

The anterior segment observation system 5 is configured to acquire a moving image of an anterior segment of the subject's eye E. In an optical system passing through the anterior segment observation system 5, an imaging plane of an imaging element 59 is arranged at the pupil conjugate position. An anterior segment illumination light source 50 irradiates illumination light (for example, infrared light) on the anterior segment of the subject's eye E. Light reflected from the anterior segment of the subject's eye E passes through an objective lens 51, is transmitted through a dichroic mirror 52, passes through an aperture part formed in a diaphragm (telecentric diaphragm) 53, is transmitted through a half mirror 23, passes through relay lenses 55 and 56, and is transmitted through a dichroic mirror 76. The dichroic mirror 52 combines (or separates) the optical path of the refractometry optical system with the optical path of the anterior segment observation system 5. The dichroic mirror 52 is disposed so that its optical path combining surface for combining these optical paths is inclined with respect to the optical axis of the objective lens 51. The light penetrating the dichroic mirror 76 forms an image on an imaging surface of the imaging element 59 (area sensor) by an imaging lens 58. The imaging element 59 performs an imaging and a signal outputting at a predetermined rate. The output (video signal) of the imaging element 59 is input to the processing unit (processor) 9 described after. The processing unit 9 displays an anterior segment image E' based on this video signal on a display screen 10a of a display unit 10 described after. The anterior segment image E' is an infrared moving image for example.

(Z Alignment System 1)

The Z alignment system 1 is configured to project light (infrared light) for performing alignment in an optical axis direction (front-back directions, Z direction) of the anterior segment observation system 5 onto the subject's eye E. Light emitted from a Z alignment light source 11 is projected onto a cornea Cr of the subject's eye E, is reflected by the cornea Cr, and forms an image on a sensor surface of a line sensor 13 by an imaging lens 12. When the position of a corneal apex changes in the optical axis direction of the anterior segment observation system 5, the projection position of the light onto the sensor surface of the line sensor 13 changes. The processing unit 9 obtains a position of the corneal apex of the subject's eye E based on the projection position of the light onto the sensor surface of the line sensor 13 and controls a mechanism for moving the optical system to perform Z alignment based on this.

(XY Alignment System 2)

The XY alignment system 2 is configured to project light (infrared light) for performing alignment in a direction (left-right directions (X direction), up-down directions (Y direction)) orthogonal to the optical axis direction of the anterior segment observation system 5 onto the subject's eye E. The XY alignment system 2 includes a XY alignment light source 21 and a collimator lens 22 that are provided in an optical path branched from the optical path of the anterior segment observation system 5 by the half mirror 23. The light emitted from the XY alignment light source 21 passes through the collimator lens 22, is reflected by the half mirror 23, and is projected onto the subject's eye E through the anterior segment observation system 5. Reflected light from the cornea Cr of the subject's eye E is guided to the imaging element 59 through the anterior segment observation system 5.

An image (bright spot image) Br based on the reflected light is included in the anterior segment image E'. The processing unit 9 controls the display unit to display an alignment mark AL and the anterior segment image E' including the bright spot image Br on the display screen of the display unit. In the case of performing XY alignment manually, a user can perform an operation for moving the optical system so as to guide the bright spot image Br in the alignment mark AL. In the case of performing XY alignment automatically, the processing unit 9 controls a mechanism for moving the optical system so as to cancel a displacement of the bright spot image Br with respect to the alignment mark AL.

(Placido Ring Projection System 3)

The placido ring projection system 3 is configured to project a concentric plurality of ring-shaped light fluxes (infrared light, placido rings) for measuring a shape of the cornea Cr of the subject's eye E onto the cornea Cr. Each ring-shaped light flux may be an arc-like light flux or a circumferential light flux. A placido plate 31 is disposed in the vicinity of the objective lens 51. In the placido plate 31, a concentric plurality of light transmitting parts (ring patterns) are formed. A placido ring light source 32 including a plurality of LEDs is provided on the back side (objective lens 51 side) of the placido plate 31. By illuminating the placido plate 31 with light from the placido ring light source 32, the concentric plurality of ring-shaped light fluxes is projected onto the cornea Cr. The reflected light (placido ring image) from the cornea Cr of the subject's eye E is detected by the imaging element 59 along with the anterior segment image E'. The processing unit 9 calculates a corneal shape parameter representing a shape of the cornea Cr, by performing a known calculation based on this placido ring image.

(Refractometry Projection System 6 and Refractometry Light Reception System 7)

The refractometry optical system includes the refractometry projection system 6 and the refractometry light reception system 7 which are used for eye refractive power measurement. The refractometry projection system 6 is configured to project light flux (a ring-shaped light flux, for example) (infrared light) for measuring eye refractive power onto the fundus Ef. The refractometry light reception system 7 is configured to receive returning light of the light flux from the subject's eye E. The refractometry projection system 6 is provided in an optical path branched by a perforated prism 65 provided in an optical path of the refractometry light reception system 7. A hole part formed in the perforated prism 65 is arranged at the pupil conjugate position. In an optical system passing through the refractometry light reception system 7, the imaging surface of the imaging element 59 is arranged at the fundus conjugate position.

In some embodiments, the refractometry light source 61 is a SLD (Super Luminescent Diode) light source which is a high-intensity light source. The refractometry light source 61 is movable in an optical axis direction. The refractometry light source 61 is arranged at the fundus conjugate position. Light emitted from the refractometry light source 61 passes through the relay lens 62 and is incident on a conical surface of the conical prism 63. The light incident on the conical surface is deflected and emits from a bottom surface of the conical prism 63. The light emitted from the bottom surface of the conical prism 63 passes through a ring-shaped light transmission part formed in a ring diaphragm 64. The light (ring-shaped light flux) passing through the light transmission part of the ring diaphragm 64 is reflected on a reflective surface formed around the hole part of the perforated prism 65, passes through a rotary prism 66, and is reflected by the dichroic mirror 67. The light reflected by the dichroic mirror 67 is reflected by the dichroic mirror 52, passes through the objective lens 51, and is projected onto the fundus Ef. The rotary prism 66 is used for averaging the light quantity distribution of the ring-shaped light flux with respect to the blood vessel or the diseased site of the fundus Ef or for reducing the speckle noise caused by the light source.

Returning light of the ring-shaped light flux projected onto the fundus Ef passes through the objective lens 51, and is reflected by the dichroic mirrors 52 and 67. The returning light reflected by the dichroic mirror 67 passes through the rotary prism 66, passes through the hole part of the perforated prism 65, passes through a relay lens 71, is reflected by a reflective mirror 72, and passes through a relay lens 73 and a focusing lens 74. The focusing lens 74 is movable along an optical axis of the refractometry light reception system 7. The light passing through the focusing lens 74 is reflected by the reflective mirror 75, is reflected by a dichroic mirror 76, and forms an image on the imaging surface of the imaging element 59 by the imaging lens 58. The processing unit 9 calculates a refractive power value of the subject's eye E by performing the known calculation based on the output of the imaging element 59. For example, refractive power value includes a spherical power, an astigmatic power, and an astigmatic axis angle, or an equivalent spherical power.

(Fixation Projection System 4)

The OCT optical system 8, which will be described after, is provided in the optical path wavelength-separated from the optical path of the refractometry optical system by the dichroic mirror 67. The fixation projection system 4 is provided in the optical path branched from the optical path of the OCT optical system 8 by the dichroic mirror 83.

The fixation projection system 4 is configured to present a fixation target to the subject's eye E. A fixation unit 40 is disposed in the optical path of the fixation projection system 4. The fixation unit 40 is movable along an optical axis of the fixation projection system 4 under the control of the processing unit 9 described after. The fixation unit 40 includes a liquid crystal panel 41.

Under the control of the processing unit 9, the liquid crystal panel 41 displays a pattern representing the fixation target. The liquid crystal panel 41 can selectively display a plurality of fixation target patterns corresponding to the types of measurement. The plurality fixation target patterns include patterns having different visual angles. The liquid crystal panel 41 can superimpose and display two or more fixation target patterns.

By changing the display position of the fixation target on the screen of the liquid crystal panel 41, the fixation position of the subject's eye E can be changed. Examples of the fixation position of the subject's eye E include a position for acquiring an image centered at a macular region of the fundus Ef, a position for acquiring an image centered at an optic disc, and a position for acquiring an image centered at the fundus center between the macular region and the optic disc. The display position of the pattern representing the fixation target can be arbitrarily changed.

Light from the liquid crystal panel 41 passes through a relay lens 42, penetrates a dichroic mirror 83, passes through a relay lens 82, is reflected by a reflective mirror 81, penetrates a dichroic mirror 67, and is reflected by the dichroic mirror 52. The light reflected by the dichroic mirror 52 passes through the objective lens 51 and is projected onto a fundus Ef. In some embodiment, each of the liquid crystal panel 41 and the relay lens 42 is independently movable in the optical axis direction.

In some embodiments, instead of the liquid crystal panel 41, a transmissive or reflective visual target chart, an illumination light source for illuminating the visual target chart, and a point light source are provided. On the visual target chart, a first fixation target pattern representing a fixation target for refractometry is printed. The fixation target for refractometry is presented to the subject's eye E by illuminating the visual target chart using the illumination light source. The two or more visual target charts, on which the fixation target patterns having different visual angles each other are printed, may be selectively illuminated by the illumination light source so that the two or more fixation targets having different visual angles each other are selectively presented to the subject's eye E. By turning on the point light source, the fixation target for OCT measurement is presented to the subject's eye E. On the visual target chart, a second fixation target pattern representing a fixation target for OCT measurement may be printed.

(OCT Optical System 8)

The OCT optical system 8 is an optical system for performing OCT measurement. The position of the focusing lens 87 is adjusted so that an end face of an optical fiber f1 and a photographing site (fundus Ef or the anterior segment) are optically conjugate with each other based on the result of the refractometry performed before the OCT measurement.

The OCT optical system 8 is provided in the optical path wavelength-separated from the optical path of the refractometry optical system by the dichroic mirror 67. The optical path of the above fixation projection system 4 is coupled with the optical path of the OCT optical system 8 by the dichroic mirror 83. Thereby, the optical axes of the OCT optical system 8 and the fixation projection system 4 can be coupled coaxially.

Figure 3:
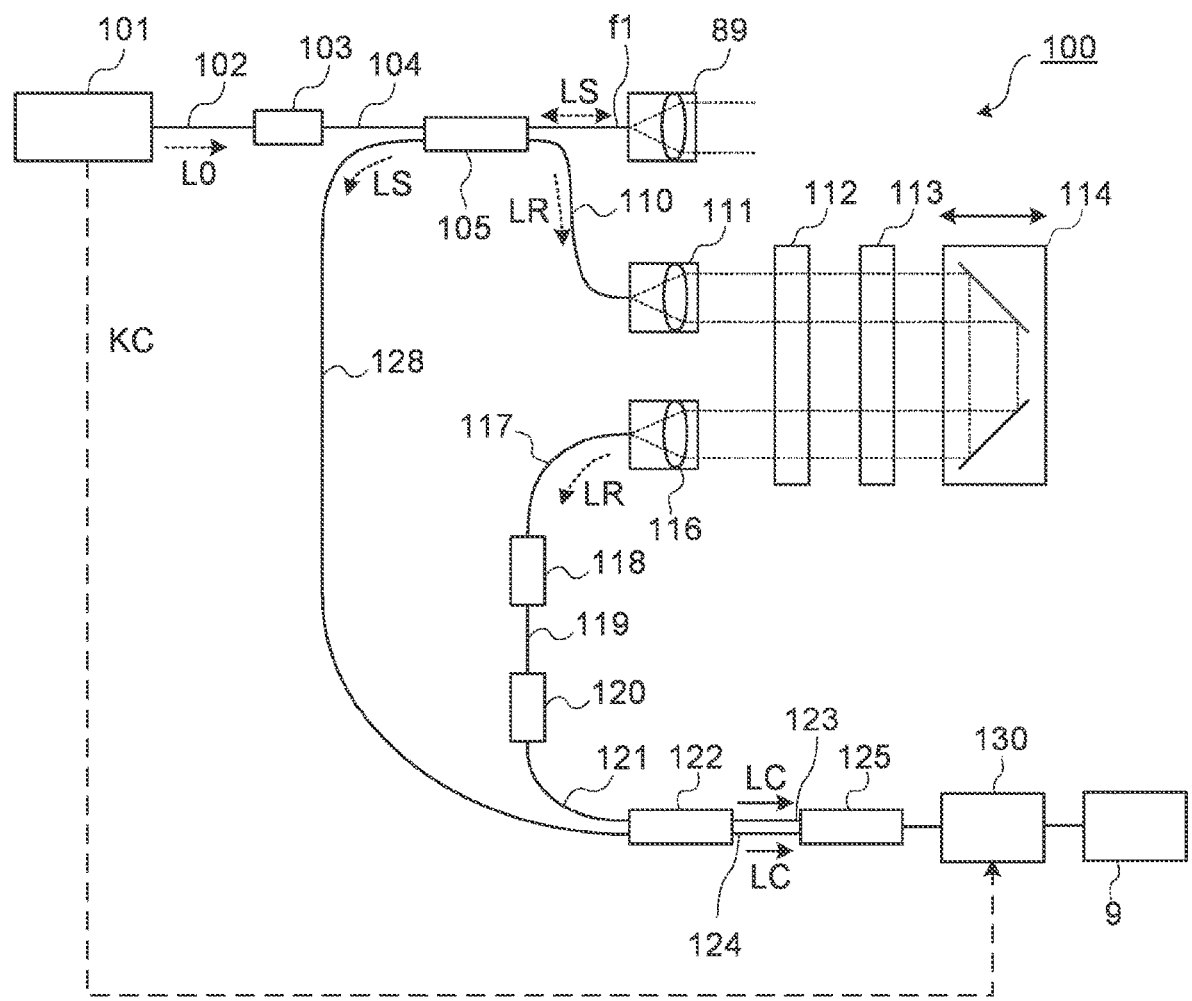
FIG. 3 is a schematic diagram illustrating an example of the configuration of the optical system of the ophthalmologic apparatus according to the embodiments.

The OCT optical system 8 includes an OCT unit 100. As illustrated in FIG. 3, in the OCT unit 100, like general swept-source-type OCT apparatuses, the OCT light source 101 includes a wavelength tunable type (a wavelength scanning type) light source capable of sweeping (scanning) the wavelengths of emitted light. The wavelength tunable type light source includes a laser light source that includes a resonator. The OCT light source 101 temporally changes the output wavelength in the near infrared wavelength band which cannot be visually recognized by the human eye.

As illustrated by an example in FIG. 3, the OCT unit 100 is provided with an optical system for performing swept source OCT. This optical system includes an interference optical system. This interference optical system has a function that splits light from the wavelength tunable type (wavelength scanning type) light source into measurement light and reference light, a function that makes the returning light of the measurement light from the subject's eye E and the reference light having traveled through a reference optical path interfere with each other and generates interference light, and a function that detects the interference light. The detection result (detection signal, interference signal) of the interference light obtained by the interference optical system is a signal indicating a spectrum of the interference light, and is sent to the processing unit 9.

The OCT light source 101 includes a near-infrared tunable laser which changes the wavelength of the emitted light (a wavelength range of 1000 nm to 1100 nm) at high speed, for example. The light L0 output from the OCT light source 101 is guided to the polarization controller 103 through the optical fiber 102, and the polarization state of the light L0 is adjusted. The light L0 whose polarization state has been adjusted is guided to the fiber coupler 105 through the optical fiber 104. The fiber coupler 105 splits the light L0 into the measurement light LS and the reference light LR.

The reference light LR is guided to the collimator 111 through the optical fiber 110. The reference light LR is converted into a parallel light beam by the collimator 111. Then, the reference light LR is guided to the corner cube 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The corner cube 114 is movable in the incident direction of the reference light LR. With this, the length of the optical path of the reference light LR is changed.

The reference light LR that has traveled through the corner cube 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through the optical fiber f1, is made into the parallel light beam by the collimator lens unit 89, is reflected by the dichroic mirror 83 via an optical scanner 88, the focusing lens 87, a relay lens 85, and a reflective mirror 84.

The optical scanner 88 is disposed at the pupil conjugate position, for example. The optical scanner 88 deflects the measurement light LS in a one-dimensionally or two-dimensional manner. The optical scanner 88 includes a first galvano mirror and a second galvano mirror, for example. The first galvano mirror deflects the measurement light LS so as to scan the photographing site (fundus Ef or the anterior segment) in a horizontal direction orthogonal to the optical axis of the OCT optical system 8. The second galvano mirror deflects the measurement light LS deflected by the first galvano mirror so as to scan the photographing site in a vertical direction orthogonal to the optical axis of the OCT optical system 8. In some embodiments, an intermediate position between the first galvano mirror and the second galvano mirror is disposed at the pupil conjugate position. Examples of scan modes with the measurement light LS performed by the optical scanner 88 like this include horizontal scan, vertical scan, cross scan, radial scan, circle scan, concentric scan, helical (spiral) scan, and the like.

The measurement light LS reflected by the dichroic mirror 83 passes through the relay lens 82, is reflected by the reflective mirror 81, is transmitted through the dichroic mirror 67, is reflected by the dichroic mirror 52, is refracted by the objective lens 51, and is incident on the subject's eye E. The measurement light LS is scattered and reflected at various depth positions of the subject's eye E. The returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC is guided to a detector 125 through optical fibers 123 and 124, respectively.

The detector 125 is a balanced photodiode, for example. The balanced photodiode includes a pair of photodetectors in which each photodiode detects each of the pair of interference light LC. The balanced photodiode outputs the difference between a pair of detection results acquired by the pair of photodetectors. The detector 125 sends the output (detection signal) to a DAQ (data acquisition system) 130.

The DAQ 130 is fed with a clock KC from the OCT light source 101. The clock KC is generated in the OCT light source 101 in synchronization with the output timing of each wavelength within a predetermined wavelength range performed by the wavelength tunable type light source. For example, the OCT light source 101 optically delays one of the two pieces of branched light obtained by branching the light L0 of each output wavelength, and then generates the clock KC based on the result of the detection of the combined light of the two pieces of branched light. The DAQ 130 performs sampling the detection signal input from the detector 125 based on the clock KC. The DAQ 130 sends the result of sampling the detection signal from the detector 125 to an arithmetic processor 220 of the processing unit 9. For example, the arithmetic processor 220 performs the Fourier transform, etc. on the spectral distribution based on the sampling data for each series of wavelength scanning (i.e., for each A line). With this, the reflection intensity profile for each A line is formed. In addition, the arithmetic processor 220 forms image data by applying imaging processing to the reflection intensity profiles of the respective A lines.

In the present example, the corner cube 114 is provided for changing the length of the optical path of the reference light LR (reference optical path, reference arm); however, the difference between the measurement optical path length and the reference optical path length may be changed using another kind of optical member.

It should be noted that the ophthalmologic apparatus 100 may include a front lens capable of inserting and removing between the subject's eye E and the objective lens 51. For example, when the OCT measurement is performed on the anterior segment, the front lens is arranged between the subject's eye E and the objective lens 51. When the OCT measurement is performed on the fundus, the front lens is removed from between the subject's eye E and the objective lens 51. In some embodiments, the ophthalmologic apparatus 100 does not include the front lens capable of inserting and removing between the subject's eye E and the objective lens 51, and is configured to be capable of performing OCT measurement on the anterior segment and the fundus by moving a part of lenses in the OCT optical system 8 in the optical axis direction.

The processing unit 9 calculates the refractive power value from the result of the measurement obtained using the refractometry optical system, and controls the refractometry light source 61 and the focusing lens 74 to move respectively to positions where the fundus Ef, the refractometry light source 61, and the imaging element 59 are conjugate with each other, in the optical axis direction based on the calculated refractive power value. In some embodiments, the processing unit 9 controls the focusing lens 87 of the OCT optical system 8 to move in its optical axis direction in conjunction with the movement of the focusing lens 74. In some embodiments, the processing unit 9 controls the liquid crystal panel 41 (fixation unit 40) to move in the optical axis direction in conjunction with the movement of the refractometry light source 61 and the focusing lens 74.

<Configuration of Processing System>

Figure 4:
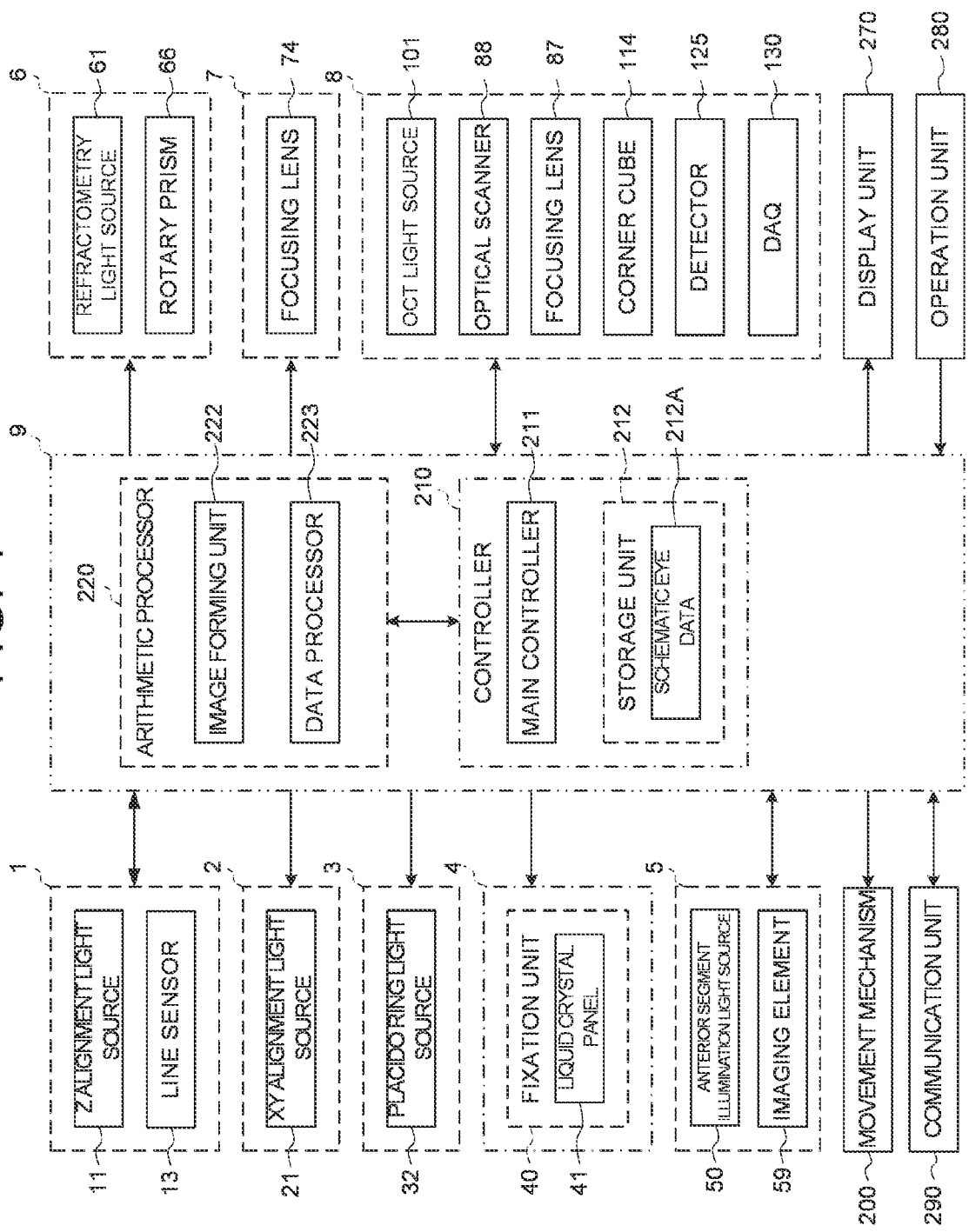
FIG. 4 is a schematic diagram for explaining a processing system of the ophthalmologic apparatus of the embodiments.
Figure 5:
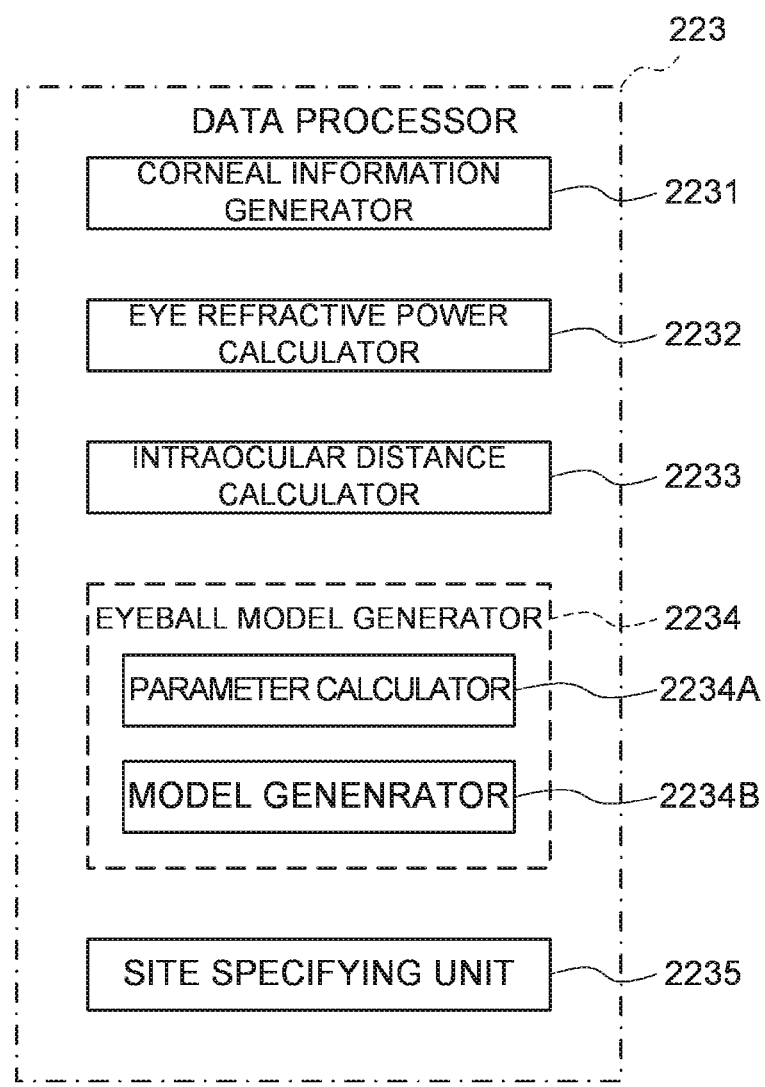
FIG. 5 is a schematic diagram for explaining a processing system of the ophthalmologic apparatus of the embodiments.

The processing system of the ophthalmologic apparatus 1000 will be described. FIGS. 4 to 5 show examples of the functional configuration of the processing system of the ophthalmologic apparatus 1000. FIG. 4 shows an example of a functional block diagram illustrating the processing system of the ophthalmologic apparatus 1000. FIG. 5 shows an example of a functional block diagram of a data processor 223.

The processing unit 9 controls each part of the ophthalmologic apparatus 1000. Further, the processing unit 9 is capable of performing various types of arithmetic processing. The processing unit 9 includes a processor. The function of the processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The processing unit 9 realizes the function according to the embodiments, for example, by reading out a computer program stored in a storage circuit or a storage device and executing the computer program.

The processing unit 9 is an example of the "ophthalmologic information processing apparatus" according to the embodiments. That is, the program for realizing the function of the processing unit 9 is an example of the "ophthalmologic information processing program" according to the embodiments.

The processing unit 9 includes a controller 210 and the arithmetic processor 220. Further, the ophthalmologic apparatus 1000 includes a movement mechanism 200, a display unit 270, an operation unit 280, and a communication unit 290.

The movement mechanism 200 is a mechanism for moving a head unit in front, back, left and right directions, the head unit housing the optical systems such as the Z alignment system 1, the XY alignment system 2, the placido ring projection system 3, the fixation projection system 4, the anterior segment observation system 5, the refractometry projection system 6, the refractometry light reception system 7, the OCT optical system 8, and the like. For example, the movement mechanism 200 is provided with an actuator that generates driving force for moving the head unit and a transmission mechanism that transmits the driving force to the head unit. The actuator is configured by a pulse motor, for example. The transmission mechanism is configured by a combination of gears, a rack and pinion, and the like, for example. The controller 210 (main controller 211) controls the movement mechanism 200 by sending a control signal to the actuator.

(Controller 210)

The controller 210 includes a processor and controls each part of the ophthalmologic apparatus. The controller 210 includes the main controller 211 and a storage unit 212. The storage unit 212 stores, in advance, a computer program for controlling the ophthalmologic apparatus. The computer program includes programs for controlling light source, programs for controlling detector, programs for controlling optical scanner, programs for controlling optical system, programs for arithmetic processing, programs for user interface, and the like. The main controller 211 operates according to the computer programs, and thereby the controller 210 performs the control processing.

The main controller 211 performs various controls of the ophthalmologic apparatus, as a measurement controller. Examples of control for the Z alignment system 1 include control of the Z alignment light source 11, control of the line sensor 13, and the like. Examples of the control of the Z alignment light source 11 include turning on and off of the light source, adjustment of an amount of light, adjustment of aperture, and the like. Examples of the control of the line sensor 13 include adjustment of exposure of a detecting element, adjustment of gain of the detecting element, adjustment of detecting rate of the detecting element, and the like. Thereby, the Z alignment light source 11 can be switched between lighting and non-lighting or the amount of light can be changed. The main controller 211 acquires a signal detected by the line sensor 13 and specifies the projection position of light onto the line sensor 13 based on the acquired signal. The main controller 211 obtains a position of a corneal apex of the subject's eye E based on the specified projection position and controls the movement mechanism 200 based on the specified position to move the head unit in front and back directions (Z alignment).

Examples of control for the XY alignment system 2 include control of the XY alignment light source 21, and the like. Examples of the control of the XY alignment light source 21 include turning on and off of the light source, adjustment of an amount of light, adjustment of aperture, and the like. Thereby, the XY alignment light source 21 can be switched between lighting and non-lighting, or the amount of light can be changed. The main controller 211 acquires a signal detected by the imaging element 59, and specifies a position of a bright spot image on the basis of returning light of the light from the XY alignment light source 21 based on the acquired signal. The main controller 211 controls the movement mechanism 200 to move the head unit in left, right, up, down directions so as to cancel a displacement the position of the bright spot image with respect to a predetermined target position (for example, a center position of the alignment mark AL) (XY alignment).

Examples of control for the placido ring projection system 3 include control of the placido ring light source 32, and the like. Examples of the control of the placido ring light source 32 include turning on and off of the light source, adjustment of an amount of light, adjustment of aperture, and the like. Thereby, the placido ring light source 32 can be switched between lighting and non-lighting, or the amount of light can be changed. In addition, the number of rings of the placido ring may be changed by controlling the placido ring light source 32. The main controller 211 controls the arithmetic processor 220 to perform a known calculation on a placido ring image detected by the imaging element 59. Thereby, corneal shape parameters of the subject's eye E are obtained.

Examples of control for the fixation projection system 4 include control of the liquid crystal panel 41, movement control of the fixation unit 40, and the like. Examples of the control of the liquid crystal panel 41 include displaying on and off of the pattern representing the fixation target, switching the patterns representing the fixation target, switching the display position of the pattern representing the fixation target, and the like.

For example, the fixation projection system 4 includes a movement mechanism that moves the liquid crystal panel 41 (or the fixation unit 40) in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move at least the liquid crystal panel 41 in the optical axis direction. Thereby, the position of liquid crystal panel 41 is adjusted so that the liquid crystal panel 41 and the fundus Ef are optically conjugate with each other.

Examples of the control for the anterior segment observation system 5 include control of an anterior segment illumination light source 50, control of the imaging element 59, and the like. Examples of the control of the anterior segment illumination light source 50 include turning on and off the light sources, adjustment of light amount, adjustment of apertures, and the like. Thereby, the anterior segment illumination light source 50 can be switched between lighting and non-lighting, or light amount can be changed. Example of the control of the imaging element 59 include adjustment of exposure of the imaging element 59, adjustment of gain of the imaging element 59, adjustment of detecting rate of the imaging element 59, and the like. The main controller 211 acquires a signal detected by the imaging element 59 and controls the arithmetic processor 220 to perform processing such as forming image based on the acquired signal and the like.

Examples of control for the refractometry projection system 6 include control of the refractometry light source 61, control of the rotary prism 66, and the like. Examples of the control of the refractometry light source 61 include turning on and off of the light source, adjustment of an amount of light, adjustment of aperture, and the like. Thereby, the refractometry light source 61 can be switched between lighting and non-lighting, or the amount of light can be changed. For example, the refractometry projection system 6 includes a movement mechanism that moves the refractometry light source 61 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the refractometry light source 61 in the optical axis direction. Examples of the control of the rotary prism 66 include control of rotating the rotary prism 66 and the like. For example, a rotary mechanism that rotates the rotary prism 66 is provided and the main controller 211 controls the rotary mechanism to rotate the rotary prism 66.

Examples of control for refractometry light reception system 7 include control of the focusing lens 74, and the like. Examples of the control of the focusing lens 74 include control of moving the focusing lens 74 in the optical axis direction. For example, the refractometry light reception system 7 include a movement mechanism that moves the focusing lens 74 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 74 in the optical axis direction. The main controller 211 is capable of moving the refractometry light source 61 and the focusing lens 74 in the optical axis direction respectively depending on the refractive power of the subject's eye E for example so that the refractometry light source 61 and the fundus Ef and the imaging element 59 are optically conjugate with each other.

Examples of control for the OCT optical system 8 include control of the OCT light source 101, control of the optical scanner 88, control of the focusing lens 87, control of the corner cube 114, control of the detector 125, control of the DAQ 130, and the like. Examples of the control of the OCT light source 101 includes turning on and off of the light source, adjustment of an amount of light, adjustment of aperture, and the like. Examples of the control of the optical scanner 88 include control of the scanning position and the scan range and the scanning speed by means of the first galvano mirror, control of the scanning position and the scan range and the scanning speed by means of the second galvano mirror, and the like.

Examples of the control of the focusing lens 87 include control of moving the focusing lens 87 in the optical axis direction, control of moving the focusing lens 87 to the in-focus reference position corresponding to the photographing site, control of moving the focusing lens 87 within the movement range (in-focus range) corresponding to the photographing site, and the like. For example, the OCT optical system 8 include a movement mechanism that moves the focusing lens 87 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 87 in the optical axis direction. In some embodiments, the ophthalmologic apparatus is provided with a holding member that holds the focusing lens 74 and the focusing lens 87, and the driver that drives the holding member. The main controller 211 controls the driver to move the focusing lenses 74 and 87. For example, the main controller 211 may moves the focusing lens 87 alone based on the intensity of the interference signal, after moving the focusing lens 87 in conjunction with the movement of the focusing lens 74.

Examples of the control of the corner cube 114 include control of moving the corner cube 114 along the optical path of the corner cube 114. For example, the OCT optical system 8 include a movement mechanism that moves the corner cube 114 along the optical path. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the corner cube 114 along the optical path. Examples of the control of the detector 125 include adjustment of exposure of a detecting element, adjustment of gain of a detecting element, adjustment of detecting rate of a detecting element, and the like. The main controller 211 controls the DAQ 130 to perform sampling of the signal detected by the detector 125 and controls the arithmetic processor 220 (image forming unit 222) to perform processing such as forming image based on the sampled signal and the like.

Further, as a display controller, the main controller 211 can cause the display unit 270 to display an image (anterior segment image, fundus image) of the subject's eye obtained by the imaging element 59, a graphical user interface for realizing the functions of the operation unit 280 by a touch panel, information corresponding to the processing result of the arithmetic processor 220, and the like. Examples of the processing result of the arithmetic processor 220 include an image formed by the image forming unit 222, processing result of the data processor 223, and the like.

Further, the main controller 211 performs writing of data into the storage unit 212, and readout of data from the storage unit 212.

(Storage Unit 212)

The storage unit 212 stores various types of data. Examples of the data stored in the storage unit 212 include a measurement result of the objective measurement, a measurement result of the OCT measurement, image data of a tomographic image, image data of an anterior segment image, subject's eye information, subject information, schematic eye data 212A, and the like. The subject's eye information includes information on the subject's eye such as identification information of the left eye/right eye. The subject information includes information on the subject such as patient ID, name, age of subject, gender, height, weight. In some embodiments, the subject information is an information acquired from an electronic health record. In some embodiments, the subject's eye information and/or the subject information are/is information input by the examiner or the subject using the operation unit 280.

The schematic eye data 212A includes two or more parameters constituting the eyeball model. Such parameters include a size parameter, a shape parameter and an optical parameter. The size parameter represents the size of a part or the whole of the eye. The shape parameter represents the shape of a site of the eye. The optical parameter represents the optical function of a site of the eye.

The schematic eye data 212A may be, for example, data of a known schematic eye. Examples of the schematic eye include Gullstrand's schematic eye, Helmholtz's schematic eye data, and the like. The parameter included in the schematic eye data 212A is replaced with the measured value obtained by the above-described placido measurement, the eye refractive power measurement, or the OCT measurement, and the parameter is provided for generation of the eyeball model described later.

The storage unit 212 further stores various types of programs and data to run the ophthalmologic apparatus.

(Arithmetic Processor 220)

The arithmetic processor 220 includes the image forming unit 222 and the data processor 223.

(Image Forming Unit 222)

The image forming unit 222 forms image data of a tomographic image of the fundus Ef based on a signal detected by the detector 125. That is, the image forming unit 222 forms the image data of the subject's eye E based on a detection result of the interference light LC obtained by the interference optical system. Like the conventional spectral-domain-type OCT, this process includes processes such as filtering and FFT (Fast Fourier Transform). The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

(Data Processor 223)

The data processor 223 performs various kinds of data processing (e.g., image processing) and various kinds of analysis on a tomographic image formed by the image forming unit 222. For example, the data processor 223 performs various correction processes such as brightness correction and dispersion correction of images. Further, the data processor 223 performs various types of image processing and analysis on images (anterior segment image, etc.) acquired using the anterior segment observation system 5.

The data processor 223 can form volume data (voxel data) of the subject's eye E by performing known image processing such as interpolation processing for interpolating pixels between tomographic images. In the case of displaying an image based on the volume data, the data processor 223 performs a rendering processing on the volume data so as to form a pseudo three-dimensional image viewed from a specific line-of-sight direction.

The data processor 223 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired volume data (three-dimensional data set, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (Z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

Further, the data processor 223 can build (form) the B-mode image or the front image (blood vessel emphasized image, angiogram) in which retinal blood vessels and choroidal blood vessels are emphasized (highlighted), based on data (for example, B scan image data) acquired in time series by OCT. For example, the OCT data in time series can be acquired by repeatedly scanning substantially the same site of the subject's eye E.

As shown in FIG. 5, the data processor 223 includes a corneal information generator 2231, an eye refractive power calculator 2232, an intraocular distance calculator 2233, an eyeball model generator 2234, and a site specifying unit 2235.

(Corneal Information Generator 2231)

The corneal information generator 2231 generates distribution information of the corneal information (corneal shape information) including the parameter(s) representing the shape of the cornea Cr, by performing a known calculation using the placido ring image acquired by the imaging element 59. That is, the corneal information is generated at on each of a plurality of positions on the cornea Cr.

Examples of the parameter(s) representing the shape of the cornea Cr include a corneal curvature radius, a corneal refractive power, a corneal astigmatic power, a corneal astigmatic axis direction, a corneal wavefront aberration, and the like.

For example, the corneal information generator 2231 can calculate the above parameter(s) by analyzing the height (or interval (distance)) of ring image of the acquired placido ring image.

Hereinafter, the case where the corneal information generator 2231 calculates a corneal curvature radius as the corneal information will be described. That is, the curvature radius distribution on the cornea Cr is obtained.

(Eye Refractive Power Calculator 2232)

The eye refractive power calculator 2232 analyzes a ring image (pattern image) acquired by receiving the returning light of the ring-shaped light flux (ring-shaped measurement pattern) by the imaging element 59, the ring-shaped light flux being projected onto the fundus Ef by the refractometry projection system 6.

For example, the eye refractive power calculator 2232 obtains a position of the center of gravity of the ring image from the brightness distribution in the image representing the acquired ring image, obtains brightness distributions along a plurality of scanning directions extending radially from the position of the center of gravity, and specifies a ring image from these brightness distributions. Subsequently, the eye refractive power calculator 2232 obtains an approximate ellipse of the specified ring image and obtains a spherical power, an astigmatic power, and an astigmatic axis angle by assigning a major axis and a minor axis of the approximate ellipse to a known formula. Alternatively, the eye refractive power calculator 2232 can obtain the eye refractive power parameter based on deformation and displacement of the ring image with respect to the reference pattern.

(Intraocular Distance Calculator 2233)

The intraocular distance calculator 2233 obtains one or more intraocular distances in the subject's eye E based on detection results (OCT data) of the interference light LC acquired by the OCT optical system 8. The one or more intraocular distances include an axial length (distance from the corneal apex to the retina). The position of a predetermined layer tissue (for example, inner limiting membrane) in the retina can be adopted as the position of the retina. In some embodiments, the intraocular distance calculator 2233 specifies a peak position of the detection result (interference signal) of the interference light LC corresponding to a predetermined site in the eye by analyzing the detection result of the interference light LC acquired by the OCT optical system 8, and obtains the above intraocular distance based on the distance between the specified peak positions. In some embodiments, the intraocular distance calculator 2233 further obtains a corneal thickness, an anterior chamber depth, a lens thickness, a length of vitreous cavity, a retinal thickness, a choroidal thickness, and the like.

(Eyeball Model Generator 2234)

The eyeball model generator 2234 obtains the parameter(s) (value(s)) on the subject's eye E based on detection results (OCT data) of the interference light LC acquired by the OCT optical system 8. Further, the eyeball model generator 2234 generates a three-dimensional eyeball model of the subject's eye E based on the obtained parameter(s).

The eyeball model generator 2234 obtains the parameter capable of calculating based on the result of the placido measurement, the eye refractive power measurement, or the OCT measurement among the parameters included in the above schematic eye data 212A. The eyeball model generator 2234 can adopt a parameter calculated by the intraocular distance calculator 2233, as a part of the parameters.

The eyeball model generator 2234 can obtain the above size parameter, the above shape parameter and the above optical parameter.

As described above, the size parameter represents the size of a part or the whole of the eye. Examples of the size parameter representing the size of a part of the eye include a corneal thickness, a lens thickness, an anterior chamber depth (distance between the posterior surface of cornea and the anterior surface of lens), a retinal thickness, a pupil diameter, and the like. Examples of the size parameter representing the size of whole of the eye include an axial length.

As described above, the shape parameter represents the shape of a site of the eye. The site of the eye may be, for example, an anterior surface of cornea, a posterior surface of cornea, an anterior surface of lens, a posterior surface of lens, a predetermined layer of retina, a choroid, a pupil (an iris), or the like. Further, examples of the parameter representing the shape include a curvature at one predetermined point, a curvature distribution in a predetermined range, an inclination angle, and the like.

As described above, the optical parameter represents the optical function of a site of the eye. Examples of the optical parameter include a refractive power (spherical power, astigmatic power, astigmatic axis, etc.) of cornea (anterior surface, posterior surface), a refractive power of lens (anterior surface, posterior surface), and the like. Further, the optical parameters may include any parameter related to aberration, such as chromatic aberration, spherical aberration, coma aberration, astigmatism, field curvature, distortion and the like. Further, the optical parameters may include any parameter relates to optical characteristics of a site of the eye, such as refractive index, reflectance, dispersion characteristics, and polarization property of the site of the eye.

It should be noted that a parameter included in the schematic eye data may be corrected based on the data obtained by performing the placido measurement, the eye refractive power measurement, or the OCT measurement, and may be applied as a new parameter constituting the eyeball model.

The eyeball model generator 2234 includes a parameter calculator 2234A and a model generator 2234B.

(Parameter Calculator 2234A)

The parameter calculator 2234A obtains a predetermined parameter relate to the subject's eye E by analyzing the OCT data (data set) obtained by the OCT optical system 8. The OCT data set represents a morphology (form) of three-dimensional region of the subject's eye E including a range from the anterior surface of cornea to the surface of retina. That is, this three-dimensional region corresponds to a measurement region of OCT. The image obtained using the OCT data set depicts the morphology at each part of the subject's eye E in this three-dimensional region.

Example of processing in which the size parameter is calculated from the OCT data set will be described. First, the parameter calculator 2234A specifies a site of the subject's eye E to be calculated. This processing is executed by analyzing pixel value of the OCT data set. For example, the processing includes known image processing such as filter processing, threshold value processing, and edge detection. As a typical example, when the corneal thickness is to be obtained the anterior surface of cornea and the posterior surface of cornea are specified, when the lens thickness is to be obtained the anterior surface of lens and the posterior surface of lens are specified, when the anterior chamber depth is to be obtained the posterior surface of cornea and the anterior surface of lens are specified, when the retinal thickness is to be obtained the surface of the retina and the back of the retina are specified, or when the pupil diameter is to be obtained the edge of the iris (border of the pupil) is specified. When the axial length is to be obtained from the OCT data set, the anterior surface of cornea and the surface of the retina (a predetermined layer tissue in the retina) are specified.

Next, the parameter calculator 2234A specifies two or more characteristic points as measurement positions of the size among the specified sites. This processing is executed by analyzing pixel position and/or pixel value of the specified site. For example, the processing includes known image processing such as pattern matching, differential operation (curvature operation), filter processing, threshold value processing, and edge detection. When the corneal thickness is to be obtained, the apex of the anterior surface of cornea (corneal apex) and the apex of the posterior surface of cornea are specified. The apex of the anterior surface of cornea is specified, for example, by performing shape analysis on the anterior surface of cornea, or is specified using Z coordinate value of the pixel of the anterior surface of cornea. The apex of the posterior surface of cornea is specified, for example, as an intersection between a straight line, which passes through the corneal apex and extending in the Z direction, and the posterior surface of cornea, and is specified by performing shape analysis on the posterior surface of cornea, or is specified using Z coordinate value of the pixel of the posterior surface of cornea. Similar processing is performed for other parameters.

Further, the parameter calculator 2234A obtains the size based on the two or more specified characteristic points. When the corneal thickness is to be obtained, the distance between the specified apex of the anterior surface of cornea and the specified apex of the posterior surface of cornea is obtained. This distance may be expressed, for example, by the number of pixels between two apexes, or may be a value obtained by converting the number of pixels into a real space distance based on the imaging magnification.

Example of processing in which the shape parameter is calculated from the OCT data set will be described. First, the parameter calculator 2234A specifies a site of the subject's eye E to be calculated. This processing may be similar to the case of the size parameter. Next, the parameter calculator 2234A calculates the shape parameter based on the specified site. For example, in case of obtaining curvature at the characteristic point, the characteristic point can be specified in the same manner as the size parameter, and the curvature at this characteristic point can be calculated based on the shape in the vicinity of this characteristic point. In case of obtaining the curvature distribution in a predetermined range, the same processing may be performed for each point within the range. In case of obtaining inclination angle, differential processing can be performed based on the shape at the position (point) and in the vicinity thereof.

Example of processing in which the optical parameter is calculated from the OCT data set will be described. The OCT data set represents the morphology (e.g., shape, size, etc.) of a site of the subject's eye E. With regard to optical parameters that can be calculated from the morphology of the site alone, the optical parameters can be calculated using a known formula that associates the shape and size of the site with the optical parameters. Further, with regard to optical parameters that can not be calculated from the morphology of the site alone, the optical parameters can be calculated using a known formula while referring to other necessary values (measured values or standard values such as schematic eye data). For example, in case of obtaining a refractive power of the lens, the refractive index of the lens and the refractive index of the site adjacent thereto can be referred to. Alternatively, the refractive power can be obtained by performing ray tracing assuming a paraxial approximation.

(Model Generator 2234B)

The model generator 2234B generates the three-dimensional eyeball model of the subject's eye E using the distribution of the corneal information (specifically, the curvature radius distribution) generated by the corneal information generator 2231. More specifically, the model generator 2234B generates the three-dimensional eyeball model of the subject's eye E based on the distribution of the corneal information generated by the corneal information generator 2231, the axial length calculated by the intraocular distance calculator 2233, the value of refractive power calculated by the eye refractive power calculator 2232, and the parameter(s) calculated by the parameter calculator 2234A.

The model generator 2234B associates each of the parameters calculated in the units described above with the corresponding site in the eyeball model. This processing is performed, for example, by associating a parameter with a site or a characteristic point specified in the processing of calculating it. For example, the parameters representing the shape of the anterior surface of cornea (curvature, curvature distribution, etc.) are associated with the anterior surface of cornea in the eyeball model. In the embodiments, the curvature radius distribution acquired using the placido ring projection system 3 is associated with the cornea in the eyeball model. Further, the parameter representing the axial length is associated with the anterior surface of cornea (corneal apex, etc.) and the retinal surface (central fovea, etc.) in the eyeball model. The same applies to other parameters.

(Site Specifying Unit 2235)

The site specifying unit 2235 specifies a traveling direction in the eye of the measurement light incident on the cornea Cr, and specifies a position corresponding to an intraocular site of the subject's eye E in the traveling direction based on the OCT data acquired using the measurement light. Here, it is assumed that the intraocular site is the retina (or any of the layer tissues constituting the retina).

Figure 6:
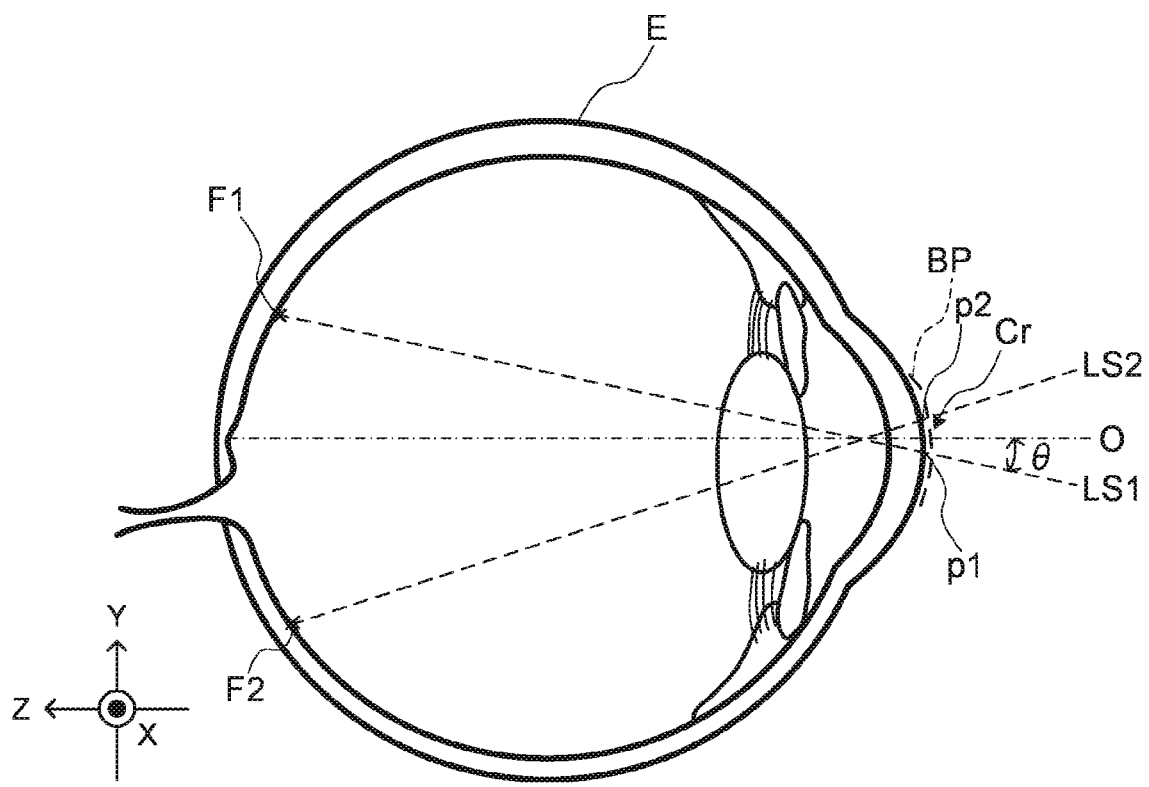
FIG. 6 is a schematic diagram for explaining an operation of the ophthalmologic apparatus according to the embodiments.
Figure 7:
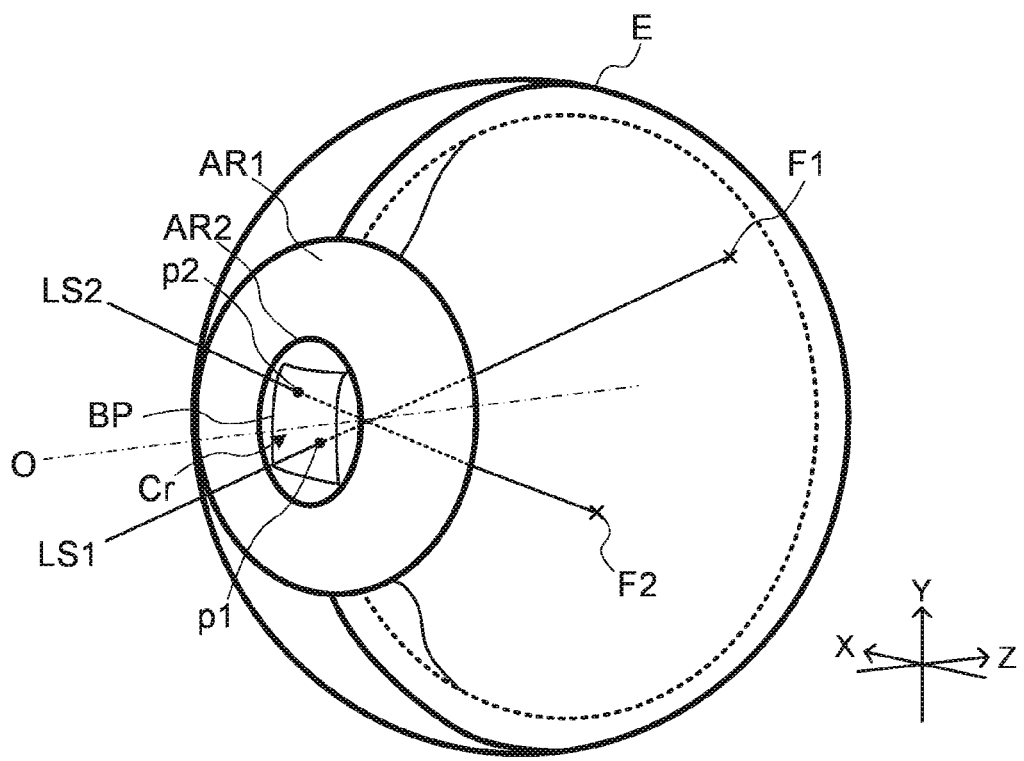
FIG. 7 is a schematic diagram for explaining an operation of the ophthalmologic apparatus according to the embodiments.

FIGS. 6 and 7 show diagrams describing the operation of the site specifying unit 2235. FIG. 6 schematically shows the measurement light incident on the subject's eye E. FIG. 7 schematically shows the measurement light incident on a plurality of positions on the cornea Cr of the subject's eye E. In FIGS. 6 and 7, the similar parts are given the same reference numerals. The same description may not be repeated.

As described above, the optical scanner 88 deflecting the measurement light is disposed at the pupil conjugate position. Thereby, the measurement light is deflected with reference to the pupil or its vicinity. Assuming that the scan angle (on the basis of the optical axis O) of the optical scanner 88 is θ as shown in FIG. 6, the site specifying unit 2235 specifies the traveling direction of the measurement light by performing ray tracing on the measurement light based on the scan angle θ of the optical scanner 88 and the eyeball model generated by the eyeball model generator 2234. The ray tracing is a known technique for tracing rays traveling through different media using Snell's law. In the embodiments, behavior of the measurement light passing through the eyeball model is obtained (determined) by geometric optically tracing the impact of the cornea, the lens, etc. of the eyeball model on the light beam.

Further the site specifying unit 2235 can specify a plurality of positions in the intraocular site by specifying the traveling direction of the measurement light incident on each of a plurality of incident positions on the cornea Cr.

As shown in FIG. 7, the curvature radius distribution BP of the cornea Cr acquired using the placido ring projection system 3 is associated with the cornea Cr on the front side of the pupil area AR2 surrounded by the iris area AR1. The site specifying unit 2235 specifies the traveling direction in the eye by performing ray tracing on the measurement light LS1 incident on the incident position p1 on the cornea Cr, and specifies the position F1 corresponding to the retina from the OCT data (A scan data) acquired using the measurement light LS1. The position corresponding to the retina can be specified by specifying a peak position of the OCT data. At this time, the ray tracing is performed using the curvature radius corresponding to the incident position p1 in the curvature radius distribution BP. The position corresponding to the retina may be any position(s) of the layer tissues constituting the retina. Examples of the layer tissue constituting the retina include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, and the like.

In the same way, the site specifying unit 2235 specifies the traveling direction in the eye by performing ray tracing on the measurement light LS2 incident on the incident position p2 on the cornea Cr, and specifies the position F2 corresponding to the retina from the OCT data acquired using the measurement light LS2. At this time, the ray tracing is performed using the curvature radius corresponding to the incident position p2 in the curvature radius distribution BP. The positions F1 and F2 are positions on the retina. Thereby, the shape of the retina can be specified by reflecting the shape of the cornea Cr.

For example, the two-dimensional shape of the retina in the B scan direction can be specified by specifying two or more positions on one B scan line on the retina. For example, the three-dimensional shape of the retina can be specified by specifying three or more positions on the two or more B scan lines on the retina.

In some embodiments, the site specifying unit 2235 may convert the specified region of the retina into a real space distance based on the imaging magnification (size information), and may specify as a shape of a substantially real size of the retina based on the schematic eye data 212A, the eye refractive power acquired using the refractometry optical system, and the axial length calculated by the intraocular distance calculator 2233 (or the parameter calculator 2234A).

In this case, the site specifying unit 2235 can specify, as a region of substantially real size, the region of the retina with reference to size information generated as follows.

The site specifying unit 2235 generates the size information using the schematic eye data 212A and the measured value(s) of the optical characteristics of the subject's eye E. The measured value(s) of the optical characteristics include(s) at least one of the eye refractive power, the axial length, and the distribution of the corneal curvature radius. The distribution of the corneal curvature radius can be obtained using the placido ring projection system 3. The eye refractive power can be obtained using the refractometry projection system 6 and the refractometry light reception system 7. The axial length can be obtained using the OCT optical system 8. Such the processing performed by the site specifying unit 2235 may be similar to the processing disclosed in Japanese Unexamined Patent Application Publication No. 2016-043155.

The site specifying unit 2235 generates the size information using the schematic eye data and the measured value acquired by the ophthalmologic apparatus 1000. In this generation processing of the size information, for a parameter which can be measured using the ophthalmologic apparatus 1000 among parameters included in the schematic eye data, the measured value(s) acquired by the ophthalmologic apparatus 1000 is (are) used.

In the embodiments, the site specifying unit 2235 can generate the size information by performing magnification correction based on the acquired measured value(s). For example, the site specifying unit 2235 obtains the magnification by the eyeball optical system of the subject's eye E, and generates the size information indicating the size for one pixel in a horizontal direction in the tomographic image of the subject's eye E from the obtained magnification.

As a specific example, first, the site specifying unit 2235 calculates the magnification by the eyeball optical system of the subject's eye based on the measured value(s) of the optical characteristics of the subject's eye E. In the embodiments, both the magnification by the subject's eye E and the magnification by the OCT optical system 8 are considered in obtaining the photographing magnification. Here, it is assumed that the OCT optical system 8 has a general configuration in which the objective lens 51, the imaging diaphragm (not shown), the variable magnification lens (focusing lens 87), and the relay lens 85 are arranged on the optical axis in order from the subject's eye E side.

First, in a case that the eye refractive power is a measured value at the corneal apex (corneal refractive power), the site specifying unit 2235 converts it into the refractive power at the pupil (pupil refractive power) as necessary. This calculation can be executed based on, for example, a spectacle wearing distance and a distance from the corneal apex to the entrance pupil as conventional.

Next, the site specifying unit 2235 calculates the imaging position by the objective lens 51. This calculation can be executed by the Newton equation based on, for example, the pupil refractive power, the focal length of the objective lens 51, and a distance from the entrance pupil to the front focal point of the objective lens 51.

Next, the site specifying unit 2235 calculates the photographing magnification by the variable magnification lens (focusing lens). This calculation can be executed by, for example, solving a quadratic equation representing a relation of the calculation result of the imaging position by the objective lens 51 and the focal distance, principal focal length and object to image distance of the variable magnification lens, for the photographing magnification.

Next, the site specifying unit 2235 calculates an exit angle from the objective lens 51. This calculation can be executed based on, for example, the result of calculation of the photographing magnification, a distance from the rear principal point of the objective lens 51 to the imaging diaphragm, and the focal distance of the objective lens 51. In this case, the exit angle is calculated so that the height of an image on the detection surface of the image becomes a predetermined value. This predetermined value is set to, for example, −0.1 mm (the minus sign indicates that the image is formed in the downward direction from the optical axis).

Next, the site specifying unit 2235 calculates an incident angle to the objective lens 51 such that the height of an image on the diaphragm surface of the imaging diaphragm becomes the abovementioned predetermined value. This calculation can be executed based on, for example, the result of calculation of the exit angle from the objective lens 51 and the angular magnification of the entrance pupil and the imaging diaphragm.

Next, in case that the distribution of the curvature radius of the anterior surface of the cornea alone is obtained by the placido measurement, the site specifying unit 2235 calculates the curvature radius of the posterior surface of the cornea of the subject's eye E. This calculation can be executed based on, for example, the measured value of the corneal curvature (curvature of the anterior surface of the cornea) measured by using the placido ring projection system 3, and the ratio between the curvatures of the anterior surface and the posterior surface of the cornea. As the ratio of the curvature, a value of the schematic eye data can be used, for example. In the case of measuring the curvature (curvature radius) of the anterior surface or the posterior surface of the cornea Cr using the OCT optical system 8, this measured value can be used as the curvature radius of the anterior surface or the posterior surface of the cornea.

Next, the site specifying unit 2235 calculates the distance from the posterior surface of the lens of the subject's eye E to the retinal surface (fundus) using the measured value of the axial length or the schematic eye data.

Next, the optical constant of the eyeball optical system of the subject's eye E is determined. Then, as the optical constant of the subject's eye E, for example, the measured value of the curvature (curvature radius) of the cornea, the measured value of the refractive power and the measured value of the axial length are adopted, and the value of the schematic eye data is adopted for measured values which can not be obtained. Further, as the distance from the posterior surface of lens to the retina (fundus), a value obtained by subtracting the measured value obtained by using the OCT optical system 8 or a standard value (value of the schematic eye data) of the distance from the anterior surface of cornea to the posterior surface of lens from the measured value of the axial length is used.

When the optical constant of the subject's eye E is determined, the site specifying unit 2235 calculates the height of an image on the retinal surface (fundus). This calculation can be executed by, for example, performing ray tracing using the determined optical constant and the result of calculation of the incident angle to the objective lens 51.

Finally, the site specifying unit 2235 calculates the magnification based on the calculation result of the height of the image on the retinal surface, the calculation result of the height of the image on the detection surface, the relay magnification of a relay lens (the influence of the imaging optical system and so on), and the like. This magnification is obtained considering the magnification of the eyeball optical system of the subject's eye E and the magnification of the imaging optical system.

The site specifying unit 2235 obtains the length (unit: micrometer/pixel) of each pixel in vertical and horizontal directions in the tomographic image from the obtained magnification, as the size information. For example, the site specifying unit 2235 includes table information in which the lengths in the vertical and horizontal directions for one pixel are associated with each of a plurality of magnifications in advance, and obtains the lengths for one pixel in vertical and horizontal directions in the tomographic image from the obtained magnification by referring to the table information. Instead of the table information on a plurality of discrete magnification values, graph information, in which a continuous change in the magnification values is associated with a change in the size for one pixel, can also be used.

When the size information is obtained as described above, the site specifying unit 2235 converts the distance between any two points specified on the retina into a distance corresponding to the actual size based on the size information.

The calculation processing of the above size information for the specified position is performed, each time the traveling direction in the eye is specified by performing ray tracing on the measurement light and the position corresponding to the position on the retina is specified from the OCT data along the specified traveling direction, as described above.

The substantially real shape of the retina reflecting the shape of the cornea Cr can be specified using the size information as described above.

(Display Unit 270, Operation Unit 280)

Upon receiving control of the controller 210, the display unit 270 displays information, as a user interface unit. The display unit 270 includes the display unit 10 as illustrated in FIG. 2 and the like.

The operation unit 280 is used to operate the ophthalmologic apparatus, as the user interface unit. The operation unit 280 includes various types of hardware keys (the joystick, buttons, switches, etc.) provided in the ophthalmologic device. Further, the operation unit 280 may include various kinds of software keys (buttons, icons, menus, etc.) displayed on the touch panel type display screen 10a.

At least part of the display unit 270 and the operation unit 280 may be integrally configured. A typical example of this is the touch-panel display screen 10a.

(Communication Unit 290)

The communication unit 290 has the function of communicating with an external device (not shown). The communication unit 290 includes a communication interface according to the mode of communication with an external device. Examples of the external device includes an eyeglass lens measurement device for measuring the optical properties of lenses. The eyeglass lens measurement device measures the power of the eyeglass lens worn by the subject, or the like and inputs the measurement data to the ophthalmologic apparatus 1000. The external device may also be a device (reader) having the function of reading information from a recording medium or a device (writer) having the function of writing information to a recording medium. Further, the external device may be a hospital information system (HIS) server, a Digital Imaging and Communications in Medicine (DICOM) server, a doctor terminal, a mobile terminal, a personal terminal, a cloud server, or the like. The communication unit 290 may be provided in the processing unit 9, for example.

The processing unit 9 (ophthalmologic information processing apparatus 400) is an example of the "ophthalmologic information processing apparatus" according to the embodiments. The OCT optical system 8 (OCT optical system 320) is an example of the "OCT measurement unit" according to the embodiments. The placido ring projection system 3 (placido ring projection system 310) and the corneal information generator 2231 are an example of the "corneal shape measurement unit" according to the embodiments. The retina is an example of the "intraocular site" according to the embodiments. The refractometry optical system (the refractometry projection system 6 and the refractometry light reception system 7) and the eye refractive power calculator 2232 are an example of the "eye refractometry unit" according to the embodiments. The schematic eye data 212A is an example of the "standard value" according to the embodiments.

<Operation Example>

The operation of the ophthalmologic apparatus 1000 according to the embodiments will be described.

Figure 8:
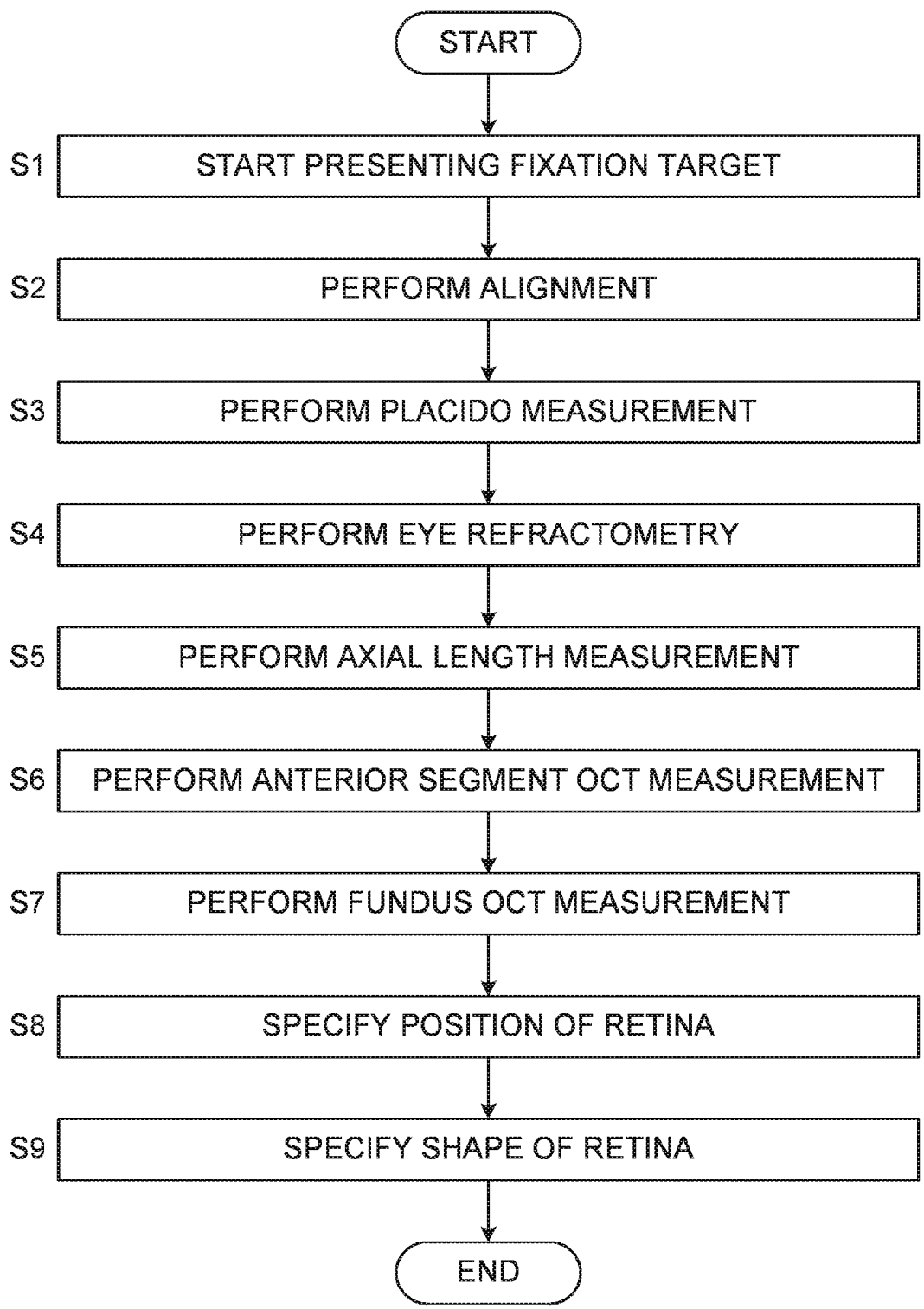
FIG. 8 is a schematic diagram illustrating a flow of the operation example of the ophthalmologic apparatus according to the embodiments.

FIG. 8 illustrates an example of the operation of the ophthalmologic apparatus 1000. FIG. 8 shows a flowchart of an example of the operation of the ophthalmologic apparatus 1000. The storage unit 212 stores computer programs for realizing the processing shown in FIG. 8. The main controller 211 operates according to the computer programs, and thereby the main controller 211 performs the processing shown in FIG. 8.

(S1: Start Presenting Fixation Target)

When the examiner performs a predetermined operation on the operation unit 280 in a state where the face of the subject is fixed to a face supporter (not shown), the ophthalmologic apparatus 1000 starts presenting the fixation target to the subject's eye E.

Specifically, the main controller 211 causes the liquid crystal panel 41 to display the fixation target pattern representing the predetermined fixation target by controlling the fixation projection system 4. Thereby, the subject's eye can be made to gaze at a predetermined fixation position.

(S2: Perform Alignment)

Sequentially, the ophthalmologic apparatus 1000 performs alignment.

Specifically, the main controller 211 turns on the Z alignment light source 11 and the XY alignment light source 21. Furthermore, the main controller 211 turns on the anterior segment illumination light source 50. The processing unit 9 acquires imaging signal of an anterior segment image formed on the imaging surface of the imaging element 59 and causes the display unit 270 to display the anterior segment image. After that, the optical system shown in FIG. 2 is moved to at the inspection position of the subject's eye E. The inspection position is a position where the inspection of the subject's eye E can be performed with sufficient accuracy. The subject's eye E is placed at the inspection position through the alignment described above (that is, by the use of the Z alignment system 1, the XY alignment system 2, and the anterior segment observation system 5). The movement of the optical system is performed by the controller 210 according to operation or instruction from a user, or instruction by the controller 210. That is, the movement of the optical system to the inspection position of the subject's eye E and the preparation for the objective measurement are carried out.

Further, the main controller 211 moves the refractometry light source 61, the focusing lens 74, and the fixation unit 40 (liquid crystal panel 41) along the respective optical axes to the origin positions (for example, the position corresponding to 0D).

(S3: Perform Placido Measurement)

Subsequently, the ophthalmologic apparatus 1000 performs placido measurement.

Specifically, the main controller 211 turns on the placido ring light source 32. When the light is emitted from the placido ring light source 32, a concentric plurality of ring-shaped light fluxes for corneal shape measurement is projected onto the cornea Cr of the subject's eye E. The corneal information generator 2231 applies arithmetic processing to the placido ring image acquired by the imaging element 59 to calculate the corneal curvature radius, and calculates the corneal refractive power, the corneal astigmatic power, and the corneal astigmatic axis angle from the calculated corneal curvature radius. The calculated corneal refractive power and the like are stored in the storage unit 212 in the controller 210.

Upon reception of an instruction from the main controller 211, an operation or instruction on the operation unit 280 by the user, the operation of the ophthalmologic apparatus 1000 proceeds to step S4.

(S4: Perform Eye Refractometry)

Next, the ophthalmologic apparatus 1000 performs eye refractometry.

Specifically, the main controller 211 causes the refractometry optical system to project the ring-shaped measurement pattern light flux for eye refractometry onto the subject's eye E as described before. The ring image based on the returning light of the measurement pattern light flux from the subject's eye E is imaged on the imaging surface of the imaging element 59. The main controller 211 determines whether or not the ring image based on the returning light from the fundus Ef detected by the imaging element 59 can be acquired. For example, the main controller 211 detects a position (pixel) of the edge of the image that is formed based on the returning light detected by the imaging element 59, and determines whether or not the width (difference between outer diameter and inner diameter) of the image is greater than or equal to a predetermined value. Alternatively, the main controller 211 may determine whether or not the ring image can be acquired by determining whether or not a ring can be formed based on points (image) having a predetermined height (ring diameter) or more.

When it is determined that the ring image can be acquired, the eye refractive power calculator 2232 analyzes the ring image based on the returning light of the measurement pattern light flux projected onto the subject's eye E by a known method, and calculates a provisional spherical power S and a provisional astigmatic power C. Based on the obtained provisional spherical power S and the obtained provisional astigmatic power C, the main controller 211 sets the refractometry light source 61, the focusing lens 74, and the fixation unit 40 (liquid crystal panel 41) to respective positions of the equivalent spherical power (S+C/2) (positions corresponding to a provisional far point).

The main controller 211 further moves the fixation unit 40 (liquid crystal panel 41) from the specified position of the equivalent spherical power (S+C/2) to a position where fogging of the subject's eye is promoted.

The main controller 211 controls the refractometry projection system 6 and the refractometry light reception system 7 to acquire a ring image again as a main measurement. The main controller 211 controls the eye refractive power calculator 2232 to calculate a spherical power, an astigmatic power, and an astigmatic axis angle from the result obtained by analyzing the ring image acquired in the same manner as described above and the movement amount of the focusing lens 74.

Further, the eye refractive power calculator 2232 obtains a position corresponding the far point of the subject's eye E (position corresponding to the far point obtained by the main measurement) from the obtained spherical power and the obtained astigmatic power. The main controller 211 moves the liquid crystal panel 41 to the position corresponding to the obtained far point. In the controller 210, the position of the focusing lens 74, the calculated spherical power, and the like are stored in the storage unit 212. Upon reception of an instruction from the main controller 211, an operation or instruction on the operation unit 280 by the user, the operation of the ophthalmologic apparatus 1000 proceeds to step S5.

When it is determined that the ring image can not be acquired, the main controller 211 moves the refractometry light source 61 and the focusing lens 74 to the minus power side (for example, −10 D) or the plus power side (for example, +10 D) in a preset step, considering the possibility of high refractive error of the eye. The main controller 211 controls the refractometry light reception system 7 to detect the ring image at each position. If it is still determined that the ring image can not be acquired, the main controller 211 executes a predetermined measurement error process. In this case, the operation of the ophthalmologic apparatus 1000 may proceed to step S5. In the controller 210, information indicating that the result of refractometry can not be acquired is stored in the storage unit 212.

(S5: Perform Axial Length Measurement)

Subsequently, the ophthalmologic apparatus 1000 performs OCT measurement for measuring the axial length.

Specifically, the main controller 211 turns on the OCT light source 101 and controls the optical scanner 88 so as to scan the subject's eye E with the measurement light LS. A detection signal obtained by scanning with the measurement light LS is fed to the data processor 223, for example. The intraocular distance calculator 2233 specifies a position corresponding to the corneal apex and a position corresponding to the retina from the acquired detection signal, and calculates the axial length based on the distance between the specified positions. In some embodiments, a detection signal obtained by scanning with the measurement light LS is fed to the image forming unit 222. The image forming unit 222 forms a B scan image of the subject's eye in which the anterior segment and the fundus Ef are depicted from the obtained detection signal. The intraocular distance calculator 2233 specifies a position corresponding to the corneal apex and a position corresponding to the retina from the B scan image formed by the image forming unit 222, and calculates the axial length based on the distance between the specified positions.

The intraocular distance calculation unit 2233 can calculate the intraocular distance such the anterior chamber depth and the lens thickness other than the axial length.

(S6: Perform Anterior Segment OCT Measurement)

Subsequently, the ophthalmologic apparatus 1000 performs anterior segment OCT measurement. In some embodiments, step S6 is executed in step S5.

In some embodiments, the operation mode of the ophthalmologic apparatus 1000 is changed to the anterior segment OCT measurement mode. In the anterior segment OCT measurement mode, the front lens is arranged between the subject's eye E and the objective lens 51, or a part of the lens in the OCT optical system 8 is moved to a position for the anterior segment OCT measurement mode in the optical axis direction.

After that, the main controller 211 turns on the OCT light source 101 and controls the optical scanner 88 so as to scan the anterior segment of the subject's eye E with the measurement light LS. With this, the three-dimensional OCT data set of the cornea is obtained.

In some embodiments, the OCT image of the anterior segment is formed from the OCT data set obtained in step S6, and the formed OCT image is displayed on the display unit 270. At this time, the OCT image of the anterior segment may be corrected based on the data obtained in step S3 or step S6.

(S7: Perform Fundus OCT Measurement)

Subsequently, the ophthalmologic apparatus 1000 performs fundus OCT measurement.

In some embodiments, the operation mode of the ophthalmologic apparatus 1000 is changed to the fundus OCT measurement mode. In the fundus OCT measurement mode, the front lens is removed from between the subject's eye E and the objective lens 51, or a part of the lens in the OCT optical system 8 is moved to a position for the fundus OCT measurement mode in the optical axis direction.

After that, the main controller 211 turns on the OCT light source 101 and controls the optical scanner 88 so as to scan the fundus of the subject's eye E with the measurement light LS. With this, the three-dimensional OCT data set of the fundus is obtained.

Sequentially, the main controller 211 controls the parameter calculator 2234A to calculate a predetermined parameter(s) using the OCT data of the anterior segment obtained in step S6 and the OCT data of the fundus obtained in step S7. After that, the main controller 211 controls the model generator 2234B to generate the eyeball model as described above.

(S8: Specify Position of Retina)

Next, the main controller 211 causes the site specifying unit 2235 to specify the traveling direction in the eye and to specify a position corresponding to the retina along the specified traveling direction, for each of the measurement light incident on a plurality of positions on the cornea Cr in the fundus OCT measurement of step S7. The site specifying unit 2235 specifies the traveling direction of the measurement light by performing ray tracing on the measurement light incident on each of the plurality of incident positions on the cornea Cr based on the incident angle of optical scanner 88 in the fundus OCT measurement of step S7 and the eyeball model acquired in step S7. Sequentially, for each measurement light, the site specifying unit 2235 specifies the position corresponding to the retina of the subject's eye E in the traveling direction based on the OCT data acquired using the measurement light.

(S9: Specify Shape of Retina)

Sequentially, for each of the plurality of positions of the retina specified in step S8, the site specifying unit 2235 converts the distance between the positions into a real space distance as described above and specifies it as a shape (form) of a real size of the retina, based on the schematic eye data 212A, the eye refractive power acquired in step S4, and the axial length calculated in step S5. Thereby, a more detailed two-dimensional or three-dimensional shape of the retina can be specified. Thus, the operation of the ophthalmologic apparatus 1000 is terminated (END).

In the above embodiments, the case has been described in which the shape of the cornea Cr is measured using the placido ring projection system 3; however, the configuration of the ophthalmologic apparatus according to the embodiments is not limited thereto. For example, a kerato visual target projection system may be provided instead of the placido ring projection system 3. In this case, the light is emitted from the kerato-ring light source, a ring-shaped light flux for corneal shape measurement is projected onto the cornea Cr of the subject's eye E. The data processor 223 can apply arithmetic processing to the image acquired by the imaging element 59 to calculate the corneal curvature radius, and can calculate the corneal refractive power, the corneal astigmatic power, and the corneal astigmatic axis angle from the calculated corneal curvature radius.

As explained above, according to the embodiments, the position and/or the shape of the retina is specified reflecting the shape of the cornea Cr of the subject's eye E. Thereby, when it is judged from the obtained tomographic image that there is an abnormality in the shape of the retina, it becomes possible to determine whether the cause is in the cornea or the real cause is in the retina. Thereby, it can contribute to the prevention of progression to pathologic myopia.

[Actions and Effects]

Described below are the actions and effects of the ophthalmologic information processing apparatus, the ophthalmologic apparatus, and the ophthalmologic information processing method according to the embodiments.

An ophthalmologic apparatus (1000) according to some embodiments includes an OCT measurement unit (OCT optical system 8, 320), a corneal shape measurement unit (placido ring projection system (3, 310) and corneal information generator 2231), an eyeball model generator (2234), and a site specifying unit (2235). The OCT measurement unit includes an optical scanner (88) and is configured to acquire data of a subject's eye by splitting light (L0) from a light source (OCT light source 101) into measurement light (LS) and reference light (LR), deflecting the measurement light using the optical scanner to project onto the subject's eye (E), and detecting interference light (LC) between returning light of the measurement light from the subject's eye and the reference light. The corneal shape measurement unit is configured to project a measurement pattern onto a cornea (Cr) of the subject's eye, to detect returning light of the measurement pattern, and to obtain curvature radius distribution on the cornea based on an image (placido ring image) formed by the detected returning light. The eyeball model generator is configured to generate an eyeball model using the curvature radius distribution on the cornea. The site specifying unit is configured to specify a traveling direction of the measurement light by performing ray tracing on the measurement light incident on each of a plurality of incident positions on the cornea based on a scan angle ($\theta$) by the optical scanner and the eyeball model, and to specify a position corresponding to an intraocular site of the subject's eye in the traveling direction based on the data acquired using the measurement light.

According to such a configuration, the curvature radius distribution on the cornea is obtained, the traveling direction of the measurement light in the eye is specified by performing ray tracing on the measurement light incident on a plurality of positions on the cornea in consideration of the curvature radius corresponding to the incident position, and the position corresponding to the intraocular site of the subject's eye in the traveling direction is specified based on the data acquired using the measurement light. Thereby, the shape of the intraocular site can be specified reflecting the shape of the cornea. Therefore, when it is judged that there is an abnormality in the shape of the intraocular site, it becomes possible to determine whether the cause is in the cornea or the real cause is in the intraocular site.

In the ophthalmologic apparatus according to some embodiments, the corneal shape measurement unit is configured to project a plurality of concentric ring-shaped light fluxes onto the cornea.

According to such a configuration, the curvature radius distribution can be easily acquired using a known corneal shape measurement optical system. Thereby, the ophthalmologic apparatus capable of specifying the shape of the intraocular site reflecting the shape of the cornea can be provided with a simple configuration.

The ophthalmologic apparatus according to some embodiments further includes an eye refractometry unit (refractometry optical system (refractometry projection system 6 and refractometry light receiving system 7) and eye refractive power calculator 2232) configured to project light onto the subject's eye, detect returning light of the light, and to obtain an eye refractive power of the subject's eye based on an image of the detected returning light and an intraocular distance calculator (2232) configured to obtain an axial length of the subject's eye based on the data acquired by the OCT measurement unit, wherein the site specifying unit is configured to specify shape of the intraocular site based on standard value data (schematic eye data 212A) representing optical characteristics of an eye, the eye refractive power, and the axial length.

According to such a configuration, the region of the specified intraocular site can be converted into a real space distance based on the imaging magnification to specify the shape of the substantially real size of the intraocular site. Thereby, it can be determined with high accuracy the presence or absence of an abnormality in the shape of the intraocular site, and, further, the shape of the intraocular site can be observed in detail.

In the ophthalmologic apparatus according to some embodiments, the eyeball model generator is configured to obtain parameter including at least one of a size parameter representing size of a part or the whole of the subject's eye, a shape parameter representing shape of a site of the subject's eye, and an optical parameter representing an optical function of a site of the subject's eye based on the data of the subject's eye acquired by the OCT measurement unit, and to generate the eyeball model based on the parameter, the standard value, the eye refractive power, the axial length, and the curvature radius distribution.

According to such a configuration, the eyeball model matched to the optical characteristics of the subject's eye can be generated using known schematic eye data. Thereby, the position of the intraocular site and the like can be specified with high accuracy.

In the ophthalmologic apparatus according to some embodiments, the intraocular site is a retina.

According to such a configuration, the shape of the retina can be specified reflecting the shape of the cornea. Thereby, when it is judged that there is an abnormality in the shape of the retina, it becomes possible to determine whether the cause is in the cornea or the real cause is in the retina.

An ophthalmologic information processing apparatus (400, processing unit 9) according to some embodiments is configured to specify at least a position of an intraocular site of a subject's eye (E) based on data acquired by performing optical coherence tomography on the subject's eye. The ophthalmologic information processing apparatus includes an eyeball model generator (2234) and a site specifying unit (2235). The eyeball model generator is configured to generate an eyeball model using curvature radius distribution on a cornea (Cr) of the subject's eye. The site specifying unit is configured to specify a traveling direction of measurement light by performing ray tracing on the measurement light incident on each of a plurality of incident positions on the cornea based on a scan angle of an optical scanner (88) deflecting the measurement light and the eyeball model, and to specify a position corresponding to an intraocular site of the subject's eye in the traveling direction based on the data acquired using the measurement light.

According to such a configuration, in consideration of the curvature radius distribution on the cornea, the traveling direction of the measurement light is specified by performing ray tracing on the measurement light incident on a plurality of positions on the cornea, and the position corresponding to the intraocular site of the subject's eye in the traveling direction is specified based on the data acquired using the measurement light. Therefore, when it is judged that there is an abnormality in the shape of the intraocular site, it becomes possible to determine whether the cause is in the cornea or the real cause is in the intraocular site.

In the ophthalmologic information processing apparatus according to some embodiments, the site specifying unit is configured to specify a shape of the intraocular site based on a standard value data (schematic eye data 212A) representing optical characteristics of an eye, a refractive power of the subject's eye, and an axial length of the subject's eye.

According to such a configuration, the region of the specified intraocular site can be converted into a real space distance based on the imaging magnification to specify the shape of the substantially real size of the intraocular site. Thereby, it can be determined with high accuracy the presence or absence of an abnormality in the shape of the intraocular site, and, further, the shape of the intraocular site can be observed in detail.

In the ophthalmologic information processing apparatus according to some embodiments, the eyeball model generator is configured to obtain parameter including at least one of a size parameter representing size of a part or the whole of the subject's eye, a shape parameter representing shape of a site of the subject's eye, and an optical parameter representing an optical function of a site of the subject's eye based on the acquired data, and to generate the eyeball model based on the parameter, the standard value, the eye refractive power, the axial length, and the curvature radius distribution.

According to such a configuration, the eyeball model matched to the optical characteristics of the subject's eye can be generated using known schematic eye data. Thereby, the position of the intraocular site and the like can be specified with high accuracy.

In the ophthalmologic information processing apparatus according to some embodiments, the intraocular site is a retina.

According to such a configuration, the shape of the retina can be specified reflecting the shape of the cornea. Thereby, when it is judged that there is an abnormality in the shape of the retina, it becomes possible to determine whether the cause is in the cornea or the real cause is in the retina.

An ophthalmologic information processing method according to some embodiments specifies a shape of an intraocular site of a subject's eye (E) based on data acquired by performing optical coherence tomography on the subject's eye. The ophthalmologic information processing method includes an eyeball model generating step and a site specifying step. The eyeball model generating step generates an eyeball model using curvature radius distribution on a cornea (Cr) of the subject's eye. The site specifying step specifies a traveling direction of measurement light by performing ray tracing on the measurement light incident on each of a plurality of incident positions on the cornea based on a scan angle of an optical scanner (88) deflecting the measurement light and the eyeball model, and specifies a position corresponding to an intraocular site of the subject's eye in the traveling direction based on the data acquired using the measurement light.

According to such a method, in consideration of the curvature radius distribution on the cornea, the traveling direction of the measurement light is specified by performing ray tracing on the measurement light incident on a plurality of positions on the cornea, and the position corresponding to the intraocular site of the subject's eye in the traveling direction is specified based on the data acquired using the measurement light. Therefore, when it is judged that there is an abnormality in the shape of the intraocular site, it becomes possible to determine whether the cause is in the cornea or the real cause is in the intraocular site.

In the ophthalmologic information processing method according to some embodiments, the site specifying step specifies shape of the intraocular site based on standard value data (schematic eye data 212A) representing an optical characteristics of an eye, an eye refractive power of the subject's eye, and an axial length of the subject's eye.

According to such a method, the eyeball model matched to the optical characteristics of the subject's eye can be generated using known schematic eye data. Thereby, the position of the intraocular site and the like can be specified with high accuracy.

<Others>

The above-described embodiments are merely examples for carrying out the present invention. Those who intend to implement the present invention can apply any modification, omission, addition, or the like within the scope of the gist of the present invention.

In some embodiments, a program for causing a computer to execute the ophthalmologic information processing method described above is provided. Such a program can be stored in any kind of recording medium that can be read by the computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus, comprising:
    an OCT measurement unit including an optical scanner and configured to acquire data of a subject's eye by splitting light from a light source into measurement light and reference light, deflecting the measurement light using the optical scanner to project onto the subject's eye, and detecting interference light between returning light of the measurement light from the subject's eye and the reference light;
    a corneal shape measurement unit including a projector and configured to project a measurement pattern onto a cornea of the subject's eye, to detect returning light of the measurement pattern, and to obtain curvature radius distribution on the cornea based on an image formed by the detected returning light;
    processing circuitry configured as an eyeball model generator configured to generate an eyeball model using the curvature radius distribution on the cornea;
    the processing circuitry further configured as a site specifying unit configured to specify a traveling direction of the measurement light by performing ray tracing on the measurement light incident on each of a plurality of incident positions on the cornea based on a scan angle by the optical scanner and the eyeball model, and to specify positions corresponding to an intraocular site of the subject's eye in the traveling direction based on the data acquired using the measurement light;
    an eye refractometry unit including a light source and configured to project light onto the subject's eye, detect returning light of the light, and obtain an eye refractive power of the subject's eye based on an image of the detected returning light; and
    the processing circuitry further configured as an intraocular distance calculator configured to obtain an axial length of the subject's eye based on the data acquired by the OCT measurement unit, wherein
    the site specifying unit is configured to generate size information based on the standard value data representing optical characteristics of an eye, the eye refractive power, and the axial length, and
    the site specifying unit is configured to specify shape of an actual size of the intraocular site by converting a distance between the specified positions into a distance corresponding to the actual size based on the size information.

2. The ophthalmologic apparatus of claim 1, wherein the corneal shape measurement unit is configured to project a plurality of concentric ring-shaped light fluxes onto the cornea.

3. The ophthalmologic apparatus of claim 1, wherein the eyeball model generator is configured to obtain parameter including at least one of a size parameter representing size of a part or the whole of the subject's eye, a shape parameter representing shape of a site of the subject's eye, and an optical parameter representing an optical function of a site of the subject's eye based on the data of the subject's eye acquired by the OCT measurement unit, and to generate the eyeball model based on the parameter, the standard value, the eye refractive power, the axial length, and the curvature radius distribution.

4. The ophthalmologic apparatus of claim 1, wherein the intraocular site is a retina.

5. An ophthalmologic information processing apparatus for specifying at least a position of an intraocular site of a subject's eye based on data acquired by performing optical coherence tomography on the subject's eye, the ophthalmologic information processing apparatus comprising:
    processing circuitry configured as an eyeball model generator configured to generate an eyeball model using curvature radius distribution on a cornea of the subject's eye; and
    the processing circuitry further configured as a site specifying unit configured to specify a traveling direction of measurement light by performing ray tracing on the measurement light incident on each of a plurality of incident positions on the cornea based on a scan angle of an optical scanner deflecting the measurement light and the eyeball model, and to specify positions corresponding to an intraocular site of the subject's eye in the traveling direction based on the data acquired using the measurement light,
    wherein the site specifying unit is configured to specify a shape of the intraocular site based on a standard value data representing optical characteristics of an eye, a refractive power of the subject's eye, and an axial length of the subject's eye, the site specifying unit is configured to generate size information based on the standard value data, the eye refractive power, and the axial length, and the site specifying unit is configured to specify shape of an actual size of the intraocular site by converting a distance between the specified positions into a distance corresponding to the actual size based on the size information.

6. The ophthalmologic information processing apparatus of claim 5, wherein the eyeball model generator is configured to obtain parameter including at least one of a size parameter representing size of a part or the whole of the subject's eye, a shape parameter representing shape of a site of the subject's eye, and an optical parameter representing an optical function of a site of the subject's eye based on the acquired data, and to generate the eyeball model based on the parameter, the standard value, the eye refractive power, the axial length, and the curvature radius distribution.

7. The ophthalmologic information processing apparatus of claim 5, wherein the intraocular site is a retina.

8. An ophthalmologic information processing method for specifying a shape of an intraocular site of a subject's eye based on data acquired by performing optical coherence tomography on the subject's eye, the ophthalmologic information processing method comprising:

an eyeball model generating step that generates an eyeball model using curvature radius distribution on a cornea of the subject's eye; and a site specifying step that specifies a traveling direction of measurement light by performing ray tracing on the measurement light incident on each of a plurality of incident positions on the cornea based on a scan angle of an optical scanner deflecting the measurement light and the eyeball model, and specifies positions corresponding to an intraocular site of the subject's eye in the traveling direction based on the data acquired using the measurement light, wherein the site specifying step specifies shape of the intraocular site based on standard value data representing an optical characteristics of an eye, an eye refractive power of the subject's eye, and an axial length of the subject's eye, the site specifying step generates size information based on the standard value data, the eye refractive power, and the axial length, and the site specifying step specifies shape of an actual size of the intraocular site by converting a distance between the specified positions into a distance corresponding to the actual size based on the size information.

* * * * *